United States Patent
Sato

(10) Patent No.: US 10,603,014 B2
(45) Date of Patent: Mar. 31, 2020

(54) ULTRASONIC DIAGNOSTIC APPARATUS, IMAGE PROCESSING APPARATUS, AND IMAGE PROCESSING METHOD

(71) Applicant: Toshiba Medical Systems Corporation, Otawara-shi (JP)

(72) Inventor: Takeshi Sato, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 468 days.

(21) Appl. No.: 14/731,534

(22) Filed: Jun. 5, 2015

(65) Prior Publication Data
US 2015/0366540 A1      Dec. 24, 2015

(30) Foreign Application Priority Data
Jun. 18, 2014    (JP) ................................ 2014-125706

(51) Int. Cl.
| A61B 8/08 | (2006.01) |
| A61B 8/00 | (2006.01) |
| G01S 15/89 | (2006.01) |

(52) U.S. Cl.
CPC ............ *A61B 8/5207* (2013.01); *A61B 8/461* (2013.01); *A61B 8/488* (2013.01); *G01S 15/8979* (2013.01)

(58) Field of Classification Search
CPC ....... A61B 8/5207; A61B 8/461; A61B 8/488; A61B 8/08; A61B 8/00; G01S 15/8979
(Continued)

(56) References Cited

U.S. PATENT DOCUMENTS

| 5,349,524 A | 9/1994 | Daft et al. |
| 5,812,992 A * | 9/1998 | de Vries ................ G06N 3/082 706/25 |

(Continued)

FOREIGN PATENT DOCUMENTS

| CN | 1644168 A | 7/2005 |
| CN | 103826541 A | 5/2014 |

(Continued)

OTHER PUBLICATIONS

Ricardo ["Adaptive Threshold and Principal Component Analysis for Features Extraction of Electrocardiogram Signals" 2014 International Symposium on Computer, Consumer and Control] (Year: 2014).*

(Continued)

*Primary Examiner* — Oommen Jacob
(74) *Attorney, Agent, or Firm* — Oblon, McClelland, Maier & Neustadt, L.L.P.

(57) ABSTRACT

An ultrasonic diagnostic apparatus includes a Doppler processing circuitry, an image generating circuitry, and a control circuitry. The Doppler processing circuitry calculates a correlation matrix using a first data string that is a set of reflected wave data generated based on reflected waves that are generated by transmitting ultrasonic waves without making time intervals of transmission pulses uniform on an identical scan line. The Doppler processing circuitry calculates a filter coefficient based on a result of principal component analysis using the correlation matrix. The Doppler processing circuitry extracts a second data string that is included in the first data string, and that is a set of reflected wave data originated from reflected waves of the ultrasonic waves that are reflected on a moving object present on the identical scan line, using the filter coefficient. The Doppler processing circuitry estimates moving object information of the moving object based on the extracted second data string.

(Continued)

The image generating circuitry generates ultrasonic image data based on the moving object information. The control circuitry causes a display to display the ultrasonic image data thereon.

9 Claims, 14 Drawing Sheets

(58) Field of Classification Search
USPC .......................................... 600/433, 453, 407
See application file for complete search history.

(56) References Cited

U.S. PATENT DOCUMENTS

| | | | | |
|---|---|---|---|---|
| 7,558,402 | B2* | 7/2009 | Zhou | G06K 9/3216 382/103 |
| 7,713,198 | B2 | 5/2010 | Sato | |
| 8,280,887 | B1* | 10/2012 | Stork | G06K 9/6219 707/737 |
| 8,306,293 | B2* | 11/2012 | Walker | G01S 7/52034 382/128 |
| 2005/0148875 | A1* | 7/2005 | Sato | A61B 8/06 600/453 |
| 2006/0079782 | A1* | 4/2006 | Beach | A61B 5/02007 600/450 |
| 2009/0297056 | A1* | 12/2009 | Lelescu | H04N 5/217 382/261 |
| 2010/0280384 | A1* | 11/2010 | Song | A61B 8/488 600/453 |
| 2012/0163691 | A1* | 6/2012 | Walker | A61B 8/00 382/131 |
| 2013/0094729 | A1* | 4/2013 | Mauldin, Jr. | G06K 9/6247 382/128 |
| 2013/0135489 | A1* | 5/2013 | Lee | H04N 17/002 348/222.1 |
| 2014/0066767 | A1* | 3/2014 | Mammone | G01S 7/52033 600/442 |
| 2015/0036877 | A1* | 2/2015 | Flanders | G06K 9/4609 382/103 |
| 2015/0110370 | A1* | 4/2015 | Solanki | G16H 30/20 382/128 |
| 2015/0130953 | A1* | 5/2015 | Mansour | G06T 7/20 348/208.1 |
| 2015/0213301 | A1* | 7/2015 | Zhao | G06K 9/00134 382/133 |
| 2015/0366540 | A1* | 12/2015 | Sato | A61B 8/5207 600/453 |

FOREIGN PATENT DOCUMENTS

| | | |
|---|---|---|
| JP | 4-197249 | 7/1992 |
| JP | 3946288 | 7/2007 |
| JP | 4504004 | 7/2010 |

OTHER PUBLICATIONS

Zhang ["Adaptive Subspace Decomposition for Hyperspectral Data Dimensionality Reduction": Proceedings 1999 International Conference on Image Processing] (Year: 1999).*

Alkaya [Variance sensitive adaptive threshold-based PCA method for fault detection with experimental application, ISA Transactions 50 (2011) 287-302] (Year: 2011).*

[A Tutorial on Principal Component Analysis, Derivation, Discussion and Singular Value Decomposition https://www.cs.princeton. edu/picasso/mats/PCA-Tutorial-Intuition_jp.pdf, 2003] (Year: 2003).*

Steinar Bjaerum et al. "Clutter Filters Adapted to Tissue Motion in Ultrasound Color Flow Imaging" IEEE Transactions on Ultrasonics, Ferroelectrics, and Frequency Control, vol. 49, No. 6, Jun. 2002, 12 pages.

Combined Office Action and Search Report dated Aug. 29, 2017 in Chinese Patent Application No. 201510335292.9 with English translation of Categories of cited documents.

* cited by examiner

| TH$_1$ | 1000000 dB |
|---|---|
| TH$_2$ | 1000000 dB |
| TH$_3$ | 20 dB |
| TH$_4$ | 15 dB |
| TH$_5$ | 10 dB |
| TH$_6$ | 5 dB |
| TH$_7$ | -1 dB |
| TH$_8$ | -1 dB |

ULTRASONIC DIAGNOSTIC APPARATUS, IMAGE PROCESSING APPARATUS, AND IMAGE PROCESSING METHOD

CROSS-REFERENCE TO RELATED APPLICATION

This application is based upon and claims the benefit of priority from Japanese Patent Application No. 2014-125706, filed on Jun. 18, 2014 the entire contents of all of which are incorporated herein by reference.

FIELD

Embodiments described herein relate generally to an ultrasonic diagnostic apparatus, an image processing apparatus, and an image processing method.

BACKGROUND

Conventionally, ultrasonic diagnostic apparatuses have been widely used to perform observation and diagnosis of blood flow of a living body. An ultrasonic diagnostic apparatus performs generation and display of blood flow information from reflective waves of ultrasonic waves by Doppler method based on the Doppler effect. The blood flow information that is generated and displayed by the ultrasonic diagnostic apparatus includes a color Doppler image, a Doppler spectrum, and the like.

The color Doppler image is an ultrasonic image that is visualized by a color flow mapping (CFM). In CFM, transmission and reception of ultrasonic waves are performed on one scan line more than one time. Furthermore, in CFM, by applying a moving target indicator (MTI) filter to a data string at the same position, a signal (clutter signal) that is originated from a static tissue or a tissue that moves slowly is suppressed, and a signal that is originated from a blood flow is thereby extracted. In CFM, blood flow information such as a speed of blood flow, a dispersion of blood flow, and a power of blood flow is estimated from this blood flow signal, and an ultrasonic image (color Doppler image) in which a distribution of estimation results is displayed, for example, in two-dimensional color image is displayed.

Usually, as an MTI filter, a filter the coefficient of which is fixed, such as a Butterworth infinite impulse response (IIR) filter and a polynomial regression filter, is used. On the other hand, an adaptive MTI filter the coefficient of which is varied according to an input signal is also known.

As one example, an adaptive MTI filter acquires a speed of a tissue from a signal before input of the MTI filter, and acquires a signal in which the phase difference is cancelled. The filter selects a coefficient according to the acquired signal from among coefficients that have been prepared in advance for the MTI filter. Moreover, an adaptive MTI filter called "eigenvector regression filter" has also been known. This adaptive MTI filter acquires a signal in which a clutter component is suppressed by a method in which an eigenvector is calculated from a correlation matrix, and a coefficient to be used for the MTI filter is directly calculated from the calculated eigenvector. This method is an applied method of a technique used in principal component analysis, a Karhunen-Loeve transform, and a characteristic space method.

In such a conventional ultrasonic color Doppler method, input data strings are often at regular intervals. The data string indicates a set of reflected wave data that is generated based on reflected waves received as a result of transmitting ultrasonic waves on the identical scan line. Furthermore, a data string being at regular intervals indicates acquisition of reflected wave data at regular intervals of time, by receiving reflected waves by transmitting ultrasonic waves to the identical scan line in such a manner that the transmission pulses are at regular intervals of time. For example, when transmission and reception of ultrasonic waves are performed for four times to one scan line, an interval of transmission and reception of ultrasonic waves between the first time and the second time, an interval of transmission and reception of ultrasonic waves between the second time and the third time, and an interval of transmission and reception of ultrasonic waves between the third time and the fourth time are equal to each other. Moreover, in the ultrasonic color Doppler method, a method applied when a data string is not at regular intervals is also disclosed. In this method, for example, clutter is approximated by performing the least square fitting of a polynomial to the data string that is not at regular intervals, and a blood flow signal is extracted by subtracting this approximation signal from an original signal. A case in which "a data string is not at regular intervals" indicates acquisition of reflected wave data that is not at regular intervals of time by receiving reflected waves by transmitting ultrasonic waves to the identical scan line in such a manner that transmission pulses are not at regular intervals of time. A "data string not being at regular interval" is described as a "data string being at irregular intervals" appropriately.

DETAILED DESCRIPTION

An ultrasonic diagnostic apparatus includes a Doppler processing circuitry, an image generating circuitry, and a control circuitry. The Doppler processing circuitry calculates a correlation matrix using a first data string that is a set of reflected wave data generated based on reflected waves that are generated by transmitting ultrasonic waves without making time intervals of transmission pulses uniform on an identical scan line. The Doppler processing circuitry calculates a filter coefficient based on a result of principal component analysis using the correlation matrix. The Doppler processing circuitry extracts a second data string that is included in the first data string, and that is a set of reflected wave data originated from reflected waves of the ultrasonic waves that are reflected on a moving object present on the identical scan line, using the filter coefficient. The Doppler processing circuitry estimates moving object information of the moving object based on the extracted second data string. The image generating circuitry generates ultrasonic image data based on the moving object information. The control circuitry causes a display to display the ultrasonic image data thereon.

Embodiments of an ultrasonic diagnostic apparatus, an image processing apparatus, and an image processing method are explained in detail below with reference to the accompanying drawings.

First Embodiment

Figure 1:
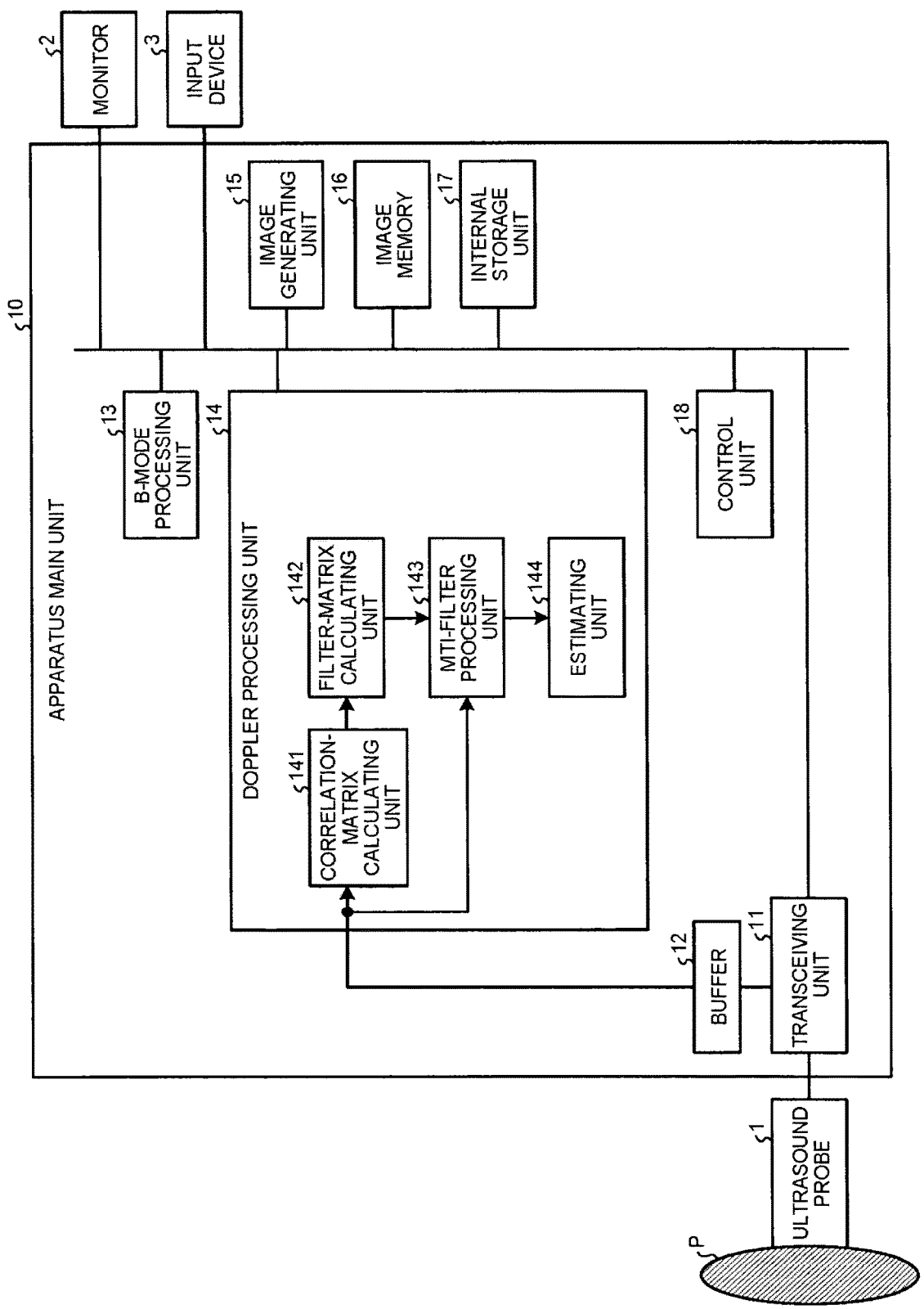
FIG. 1 is a block diagram showing a configuration example of an ultrasonic diagnostic apparatus according to a first embodiment.

First a configuration of an ultrasonic diagnostic apparatus according to a first embodiment is explained. FIG. 1 is a block diagram showing a configuration example of the ultrasonic diagnostic apparatus according to the first embodiment. As shown in FIG. 1, the ultrasonic diagnostic apparatus according to the first embodiment includes an ultrasound probe 1, a monitor 2, an input device 3, and an apparatus main unit 10.

The ultrasound probe 1 is connected to the apparatus main unit 10 to perform transmission and reception of ultrasonic waves. The ultrasound probe 1 includes, for example, multiple piezoelectric transducers, and these piezoelectric transducers generate ultrasonic waves based on a driving signal that is supplied by a transceiving unit 11 described later and included in the apparatus main unit 10. Moreover, the piezoelectric transducers included in the ultrasound probe 1 receive a reflected wave from a subject P and convert into an electric signal. Furthermore, the ultrasound probe 1 includes a matching layer that is provided for the piezoelectric transducer, a backing material to prevent propagation of an ultrasonic wave to a backward direction from the piezoelectric transducer, and the like. The ultrasound probe 1 is detachably connected to the apparatus main unit 10.

When ultrasonic waves are transmitted to the subject P from the ultrasound probe 1, the ultrasonic waves are sequentially reflected on a discontinuous surface of an acoustic impedance in a tissue of the subject P, and received by the piezoelectric transducers included in the ultrasound probe 1 as reflected wave signals. The amplitude of the received reflected wave signals is dependent on a difference in the acoustic impedance on the discontinuous surface on which the ultrasonic waves are reflected. Reflected wave signals when transmitted ultrasonic wave pulses are reflected on a surface of a moving blood flow, a cardiac wall, and the like have frequency shifts dependent on a velocity component of a moving object relative to a direction of transmission of ultrasonic waves by the Doppler effect.

The first embodiment is applicable to any of cases in which the ultrasound probe 1 is a one-dimensional (1D) array probe that two-dimensionally scans the subject P, and a mechanical four-dimensional (4D) probe or a two-dimensional (2D) array probe that three-dimensionally scans the subject P.

The input device 3 includes a mouse, a keyboard, a button, a panel switch, a touch command screen, a foot switch, a track ball, and a joy stick, and the like. The input device 3 accepts various kinds of setting requests from an operator of the ultrasonic diagnostic apparatus, and transfers the accepted various kinds of setting requests to the apparatus main unit 10.

The monitor 2 displays a graphical user interface (GUI) for an operator of the ultrasonic diagnostic apparatus to input various kinds of setting requests by using the input device 3, or displays ultrasonic image data generated in the apparatus main unit 10, and the like.

The apparatus main unit 10 is a device that generates ultrasonic image data based on a reflected wave signal received by the ultrasound probe 1. The apparatus main unit 10 includes the transceiving unit 11, a buffer 12, a B-mode processing unit 13, a Doppler processing unit 14, an image generating unit 15, an image memory 16, an internal storage unit 17, and a control unit 18 as shown in FIG. 1.

The transceiving unit 11 controls transmission and reception of ultrasonic waves performed by the ultrasound probe 1 based on a direction of the control unit 18 described later. The transceiving unit 11 includes a pulse generator, a transmission delaying circuit, a pulser, and the like, and provides a driving signal to the ultrasound probe 1. The pulse generator generates rate pulses to form transmission ultrasonic waves repeatedly at a predetermined pulse repetition frequency (PRF). Moreover, the transmission delaying circuit gives a delay time for each piezoelectric transducer that is required to converge ultrasonic waves generated by the ultrasound probe 1 into a beam form and to determine the transmission directivity to each rate pulse generated by the pulse generator. Furthermore, the pulser applies a driving signal (driving pulse) to the ultrasound probe 1 at timing based on the rate pulse. That is, the transmission delaying circuit varies delay times to be given to the respective rate pulses, thereby arbitrarily adjusting the transmission direction of ultrasonic waves that are transmitted from a surface of the piezoelectric transducer.

The transceiving unit 11 has a function enabling to change a transmission frequency, a transmission driving voltage, and the like instantaneously to execute a predetermined scan sequence based on an instruction of the control unit 18 described later. Particularly, a change of the transmission driving voltage is achieved by a linear-amplifier transmission circuit that can change the value instantaneously, or a mechanism of electrically switching multiple power supply units.

Moreover, the transceiving unit 11 includes an amplifier circuit, an analog/digital (A/D) converter, a reception delaying circuit, an adder, a quadrature detection circuit, and the like, and generates reflected wave data by performing various kinds of processing on a reflected wave signal received by the ultrasound probe 1. The amplifier circuit performs gain correction processing by amplifying a reflected wave signal per channel. The A/D converter performs A/D conversion of the reflected wave signal subjected to the gain correction. The reception delaying circuit gives a reception delay time that is required to determine the reception directivity for digital data. The adder performs addition processing of the reflected wave signals to which the reception delay time is given by the reception delaying circuit. By the addition processing by the adder, a reflection component from a direction according to the reception directivity of the reflected wave signal is emphasized.

The quadrature detection circuit converts an output signal of the adder into an in-phase signal (I-signal) and a quadrature signal (Q-signal) in a baseband. The quadrature detection circuit then stores the I-signal and the Q-signal (hereinafter, "IQ signal") in the buffer 12 as reflected wave data. The quadrature detection circuit may convert an output signal of the adder into a radio frequency (RF) signal to store in the buffer 12. The IQ signal or the RF signal is to be a signal (reception signal) including phase information. In the following, reflected wave data that is output by the transceiving unit 11 is described as a reception signal in some cases.

The transceiving unit 11 causes the ultrasound probe 1, when scanning (two-dimensionally scanning) a two-dimensional region inside the subject P, to transmit an ultrasonic beam to the two-dimensional region in the subject P. The transceiving unit 11 then generates two-dimensional reflected wave data from a reflected wave signal of the two-dimensional region received by the ultrasound probe 1. Furthermore, the transceiving unit 11 causes the ultrasound probe 1, when scanning (three-dimensionally scanning) a three-dimensional region inside the subject P, an ultrasonic beam to the three-dimensional region in the subject P from the ultrasound probe 1. The transceiving unit 11 then generates three-dimensional reflected wave data from a reflected wave signal of the three dimensional region received by the ultrasound probe 1.

The buffer 12 is a buffer that temporarily stores reflected wave data (I/Q signal) that is generated by the transceiving unit 11. Specifically, the buffer 12 stores an I/Q signal corresponding to several frames, or an I/Q signal corresponding to several volumes. For example, the buffer 12 is a first-in/first-out (FIFO) memory, and stores an I/Q signal corresponding to a predetermined number of frames. Furthermore, for example, when one frame of an I/Q signal is newly generated by the transceiving unit 11, the buffer 12 discards one frame of the I/Q signal the generated time of which is the oldest, to store the one frame of the I/Q signal that is newly generated.

The B-mode processing unit 13 and the Doppler processing unit 14 are signal processing units that perform various kinds of signal processing on reflected wave data that is generated by the transceiving unit 11 from a reflected wave signal. The B-mode processing unit 13 generates data (B-mode data) in which a signal intensity is expressed by the intensity of brightness for each of sample points, by performing logarithm amplification, envelope detection processing, logarithm compression, and the like on the reflected wave data (I/Q signal) that is read from the buffer 12.

The B-mode processing unit 13 can change a frequency band to be visualized by changing detection frequency by filter processing. By using this function of the B-mode processing unit 13, the ultrasonic diagnostic apparatus according to the first embodiment can perform harmonic imaging such as contrast harmonic imaging (CHI) and tissue harmonic imaging (THI). That is, the B-mode processing unit 13 separates reflected wave data (harmonic data or subharmonic data) of a harmonic component the reflection source of which is a contrast agent (minute bubbles, bubbles), and reflected wave data (fundamental wave data) of a fundamental wave component the reflection source of which is a tissue in the subject P, from reflected wave data of the subject P to which the contrast agent is injected. The B-mode processing unit 13 can generate B-mode data to generate contrast image data, from reflected wave data (reception signal) of a harmonic component.

The Doppler processing unit 14 generates data (Doppler data) in which movement information of a moving object in a scan range is extracted based on the Doppler effect, by performing frequency analysis on the reflected wave data that is read from the buffer 12. Specifically, the Doppler processing unit 14 generates Doppler data in which an average speed, an average dispersion value, an average power value, and the like are extracted as the movement information of a moving object for each of multiple points. The moving object is, for example, a blood stream, a tissue of a cardiac wall, and a contrast agent. The Doppler processing unit 14 according to the present embodiment generates Doppler data in which an average speed of a blood flow, an average dispersion value of the blood flow, an average power of the blood flow, and the like are estimated as movement information of the blood flow (blood flow information) at each of multiple sample points.

By using the function of the Doppler processing unit 14 described above, the ultrasonic diagnostic apparatus according to the present embodiment can perform a color Doppler method also called CFM. In CFM, transmission and reception of ultrasonic waves are performed on one scan line more than one time. Furthermore, in CFM, by applying an MTI filter to a data string at the same position, a signal (clutter signal) that is originated from a static tissue or a tissue that moves slowly is suppressed, and a signal that is originated from a blood flow is thereby extracted. In CFM, blood flow information such as a speed of blood flow, a dispersion of blood flow, and a power of blood flow is estimated from this blood flow signal. The image generating unit 15 generates ultrasonic image data (color Doppler image data) in which a distribution of estimation results is displayed, for example, in two-dimensional color image. The monitor 2 then displays the color Doppler image data.

Usually, as an MTI filter, a filter the coefficient of which is fixed, such as a Butterworth IIR filter and a polynomial regression filter, is used. On the other hand, the Doppler processing unit 14 according to the present embodiment uses an adaptive MTI filter the coefficient of which is varied according to an input signal, as the MTI filter. Specifically, the Doppler processing unit 14 according to the present embodiment uses an adaptive MTI filter called "eigenvector regression filter". Hereinafter, the "eigenvector regression filter" that is an adaptive MTI filter applying an eigenvector is described as an "eigenvector MTI filter".

The eigenvector MTI filter calculates an eigenvector from a correlation matrix, and calculates a coefficient to be used for clutter-component suppression processing from the calculated eigenvector. This method is an applied method of a technique used in principal component analysis, a Karhunen-Loeve transform, and a characteristic space method.

The Doppler processing unit 14 according to the first embodiment that uses the eigenvector MTI filter includes a correlation-matrix calculating unit 141, a filter-matrix calculating unit 142, an MTI-filter processing unit 143, and an estimating unit 144 as exemplified in FIG. 1. The correlation-matrix calculating unit 141 calculates a correlation matrix of a scan range from a data string of successive reflected wave data of the same position (same sample point). The filter-matrix calculating unit 142 calculates, for example, an eigenvalue of a correlation matrix and an eigenvector corresponding to the eigenvalue. The filter-matrix calculating unit 142 calculates a matrix in which the rank of the matrix in which respective eigenvectors are aligned based on the magnitude of the respective eigenvalues is reduced, as a filter matrix to suppress clutter components.

The MTI-filter processing unit 143 outputs a data string in which a blood flow signal originated from a blood flow is extracted from a data string of successive reflected wave data of the same position (same sample point) as a result of suppressing a clutter component by using the filter matrix. The estimating unit 144 estimates blood flow information by performing an operation such as autocorrelation operation using data that is output by the MTI-filter processing unit 143, and outputs the estimated blood flow information as Doppler data. Specific processing performed by the Doppler processing unit 14 according to the first embodiment is described in detail later.

The B-mode processing unit 13 and the Doppler processing unit 14 exemplified in FIG. 1 are capable of processing both two-dimensional reflected wave data and three-dimensional reflected wave data. That is, the B-mode processing unit 13 generates two-dimensional B-mode data from two-dimensional reflected wave data, and generates three-dimensional B-mode data from three-dimensional reflected wave data. Moreover, the Doppler processing unit 14 generates two-dimensional Doppler data from two-dimensional reflected wave data, and generates three-dimensional Doppler data from three-dimensional reflected wave data.

The image generating unit 15 generates ultrasonic image data from data that is generated by the B-mode processing unit 13 and the Doppler processing unit 14. The image generating unit 15 generates two-dimensional B-mode image data in which the intensity of reflected wave is expressed by brightness, from two-dimensional B-mode data that is generated by the B-mode processing unit 13. Furthermore, the image generating unit 15 generates two-dimensional Doppler image data in which blood flow information is visualized from two-dimensional Doppler data generated by the Doppler processing unit 14. The two-dimensional Doppler image data is speed image data, dispersion image data, power image data, or image data in which these are combined. The image generating unit 15 generates color Doppler image data in which blood flow information is displayed in color, or generates Doppler image data in which a single piece of blood flow information is displayed in a gray scale, as the Doppler image data.

Generally, the image generating unit 15 converts (scan converts) a scan-line signal string of ultrasonic scanning into a scan-line signal string of a video format represented by television and the like, to generate ultrasonic image data for display. Specifically, the image generating unit 15 generates the ultrasonic image data for display by performing coordinate transformation according to a scan form of an ultrasonic wave by the ultrasound probe 1. Moreover, the image generating unit 15 performs image processing (smoothing) to regenerate a brightness average-value image, image processing (edge enhancement) using a differential filter in an image, and the like as various kinds of image processing other than the scan conversion, by using image frames after scan conversion, for example. Furthermore, the image generating unit 15 composites character information of various kinds of parameters, scales, body marks, and the like with the ultrasonic image data.

That is, the B-mode data and the Doppler data are the ultrasonic image data before performing the scan conversion processing, and data generated by the image generating unit 15 is ultrasonic image data for display after the scan conversion processing. The B-mode data and the Doppler data are also referred to as raw data. The image generating unit 15 generates two-dimensional ultrasonic-image data for display from two-dimensional ultrasonic-image data before the scan conversion processing.

Moreover, the image generating unit 15 generates three-dimensional B-mode image data by performing coordinate transformation on three-dimensional B-mode data that is generated by the B-mode processing unit 13. Furthermore, the image generating unit 15 generates three-dimensional Doppler data by performing coordinate transformation on three-dimensional Doppler data that is generated by the Doppler processing unit 14. The image generating unit 15 generates "three-dimensional B-mode image data and three-dimensional Doppler image data" as "three-dimensional ultrasonic image data (volume data)".

Moreover, the image generating unit 15 performs rendering processing on the volume data to generate various kinds of two-dimensional image data to display the volume data on the monitor 2. As the rendering processing performed by the image generating unit 15, for example, processing in which multi planar reconstruction is performed to generate MPR image data from volume data can be considered. Furthermore, as the rendering processing performed by the image generating unit 15, for example, volume rendering processing in which two-dimensional image data reflecting tree-dimensional information is generated can be considered.

The image memory 16 is a memory that stores image data for display generated by the image generating unit 15. Moreover, the image memory 16 can also store data generated by the B-mode processing unit 13 and the Doppler processing unit 14. B-mode data and Doppler data stored in the image memory 16 can be retrieved, for example, by an operator after diagnosis, and are to be ultrasonic image data for display through the image generating unit 15. Furthermore, the image memory 16 can also store reflected wave data output by the transceiving unit 11.

The internal storage unit 17 stores a control program to perform transmission and reception of ultrasonic waves, image processing and display processing, diagnosis information (for example, patient identification (ID), observations of a doctor, and the like), or various kinds of data such as a diagnosis protocol and various kinds of body marks. Moreover, the internal storage unit 17 is also used to archive image data stored in the image memory 16, and the like as necessary. Furthermore, data stored in the internal storage unit 17 can be transferred to an external device through an interface not shown. Moreover, the internal storage unit 17 can also store data that is transferred from an external device through an interface not shown.

The control unit 16 controls overall processing of the ultrasonic diagnostic apparatus. Specifically, the control unit 18 controls processing of the transceiving unit 11, the B-mode processing unit 13, the Doppler processing unit 14, and the image generating unit 15 based on various kinds of setting requests input by an operator through the input device 3, or various kinds of control programs and various kinds of data read from the internal storage unit 17. For example, the control unit 18 controls ultrasonic wave scanning by controlling the ultrasound probe 1 through the transceiving unit 11. Usually, in CFM, B-mode image data that is tissue image data is displayed together with color Doppler image data that is blood-flow image data. To perform display thereof, the control unit 18 causes the ultrasound probe 1 to perform first ultrasonic scan to acquire blood flow information in a first scan range. The first ultrasonic scan is, for example, ultrasonic scanning to collect color Doppler image data in the Doppler mode. Furthermore, the control unit 18 causes the ultrasound probe 1 to perform second ultrasonic scan to acquire tissue condition information in a second scan range along with the first ultrasonic scan. The second ultrasonic scan is, for example, ultrasonic scanning to collect B-mode image data in B-mode.

The control unit 18 controls the ultrasound probe 1 through the transceiving unit 11 to perform the first ultrasonic scan and the second ultrasonic scan. The first scan range and the second scan range may be the same range, or the first scan range may be a smaller range than the second scan range, or the second scan range may be a smaller range than the first scan range.

Furthermore, the control unit 18 controls to display ultrasonic image data for display that is stored in the image memory 16 and the internal storage unit 17 on the monitor 2. The transceiving unit 11 and the like equipped in the apparatus main unit 10 can be configured by hardware such as an integrated circuit, and can be a program that is configured into modules as software.

Moreover, the control unit 18 controls the ultrasound probe 1 through the transceiving unit 11 to perform a scan in which color Doppler data strings are at irregular intervals. FIG. 2A to FIG. 2D are diagrams showing one example of irregular interval scan by the control unit 18 according to the first embodiment. For example, in the examples shown in FIG. 2A to FIG. 2D, each square in a horizontal direction indicates a raster direction, and each square in a vertical direction indicates a transmission and reception order. In other words, each square in the horizontal direction indicates a position of a scan line, and each square in the vertical direction indicates an elapsed time at the same position. A unit time of respective squares is the same, and is, for example, "T".

In FIG. 2A to FIG. 2D, a dotted square indicates that an ultrasonic wave is transmitted/received, and a hatched square indicates dummy data that is not used for operations although an ultrasonic wave is transmitted/received. This dummy data is to even a condition of residual multiple echoes. That is, in the irregular interval scan, only signals of dotted squares are used for operations.

Figure 2A:
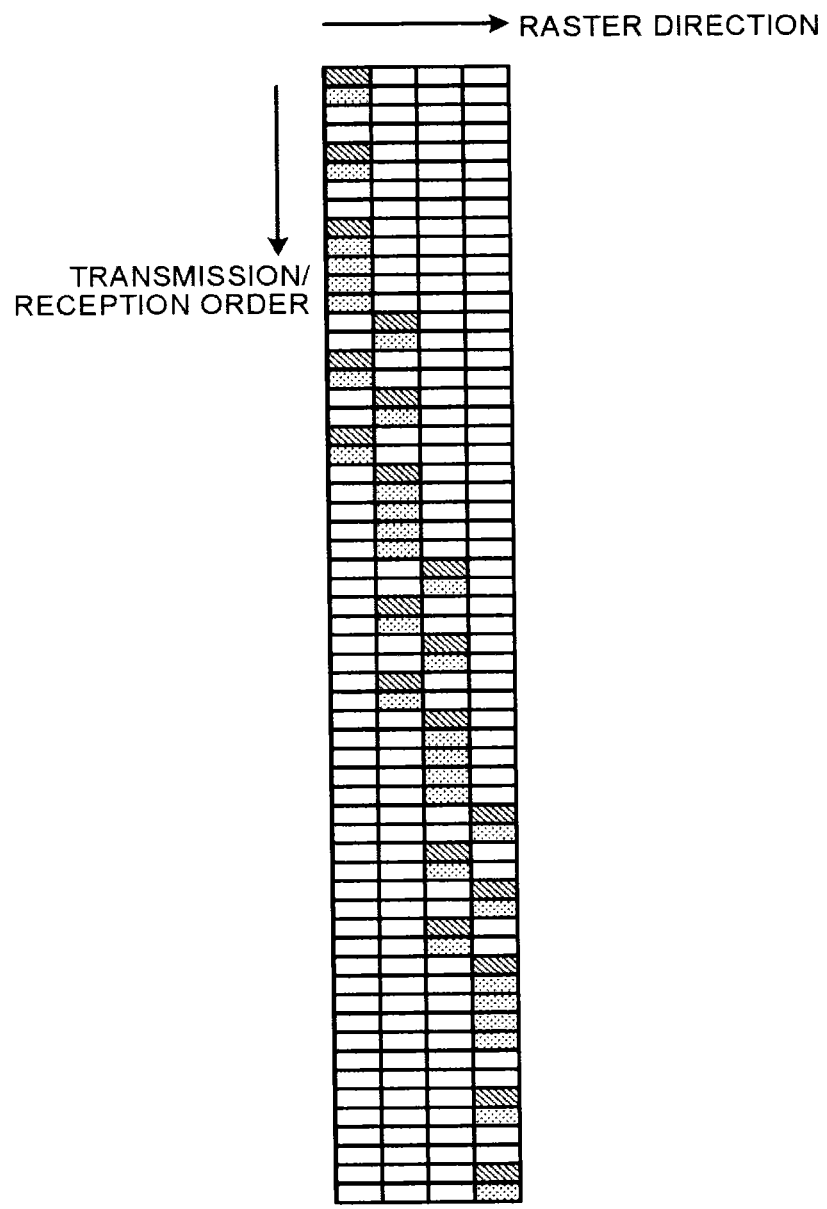
FIG. 2A is a diagram showing one example of irregular interval scan by a control unit according to the first embodiment.

When a case in which transmission/reception is performed is expressed as "o", a case of dummy data as "Δ", and a case in which transmission/reception is performed as "–" for convenience of explanation, in the example shown in FIG. 2A, it is indicated that the irregular interval scan having a pattern of "Δo--Δo--Δoooo--Δo--Δo" is performed in a raster at the left end. Moreover, in the example shown in FIG. 2A, it is indicated that the irregular interval scan having the same pattern as that of the raster at the left end starts in a next raster (the second from left) after the thirteenth transmission and reception in the raster at the left end.

Figure 2B:
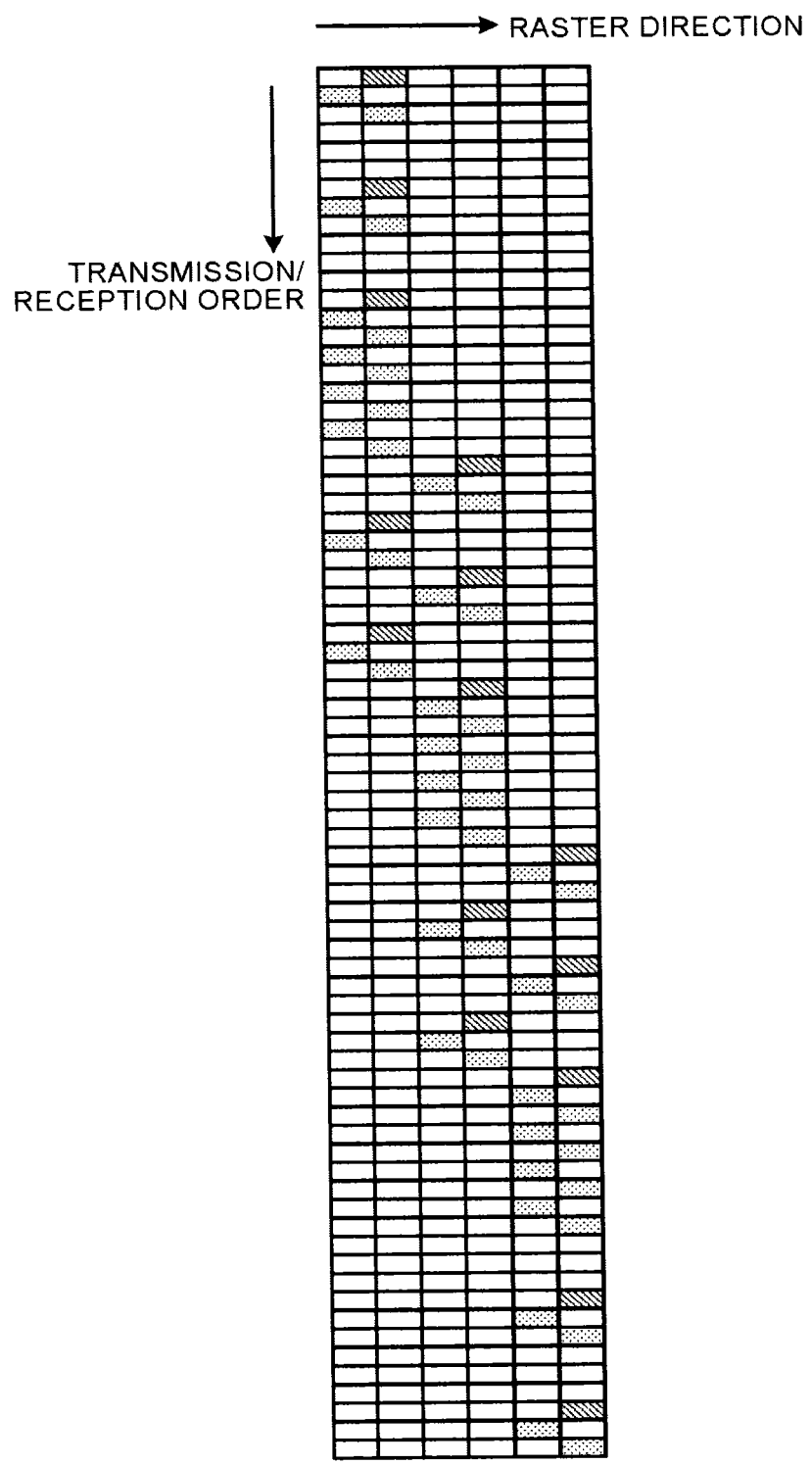
FIG. 2B is a diagram showing one example of irregular interval scan by the control unit according to the first embodiment.

Furthermore, in the example shown in FIG. 2B, it is indicated that the irregular interval scan having a pattern of "-o-----o-----o-o-o-o-----o-----o" is performed in a raster at the left end. Moreover, in the example shown in FIG. 2B, it is indicated that the irregular interval scan having a pattern of "Δ-o---Δ-o---Δ-o-o-o-o---Δ-o---Δ-o" is performed in the second raster from left.

Figure 2C:
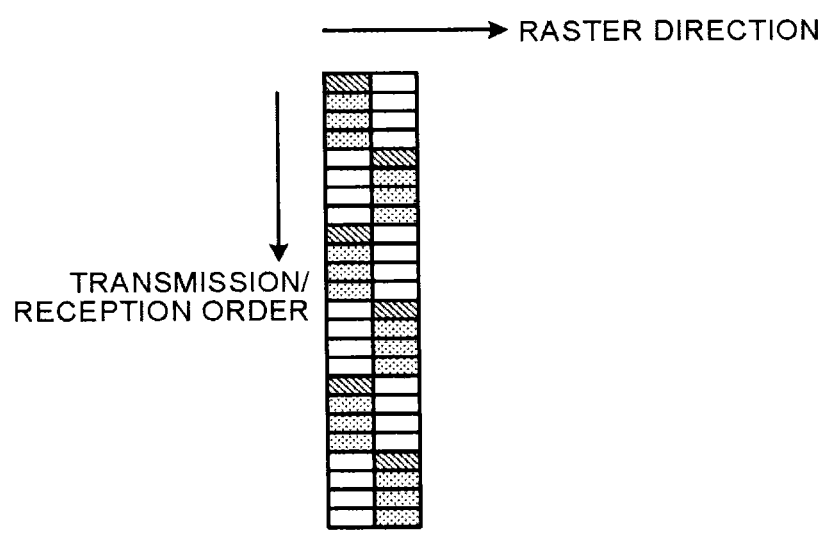
FIG. 2C is a diagram showing one example of irregular interval scan by the control unit according to the first embodiment.

Furthermore, in the example shown in FIG. 2C, it is indicated that the irregular interval scan having a pattern of "Δoooo----Δooo----Δooo" is performed in a raster at the left end. Moreover, in the example shown in FIG. 2C, it is indicated that the irregular interval scan having the same pattern as that of the raster at the left end starts in a next raster (the second from left) after the fourth transmission and reception in the raster at the left end.

Figure 2D:
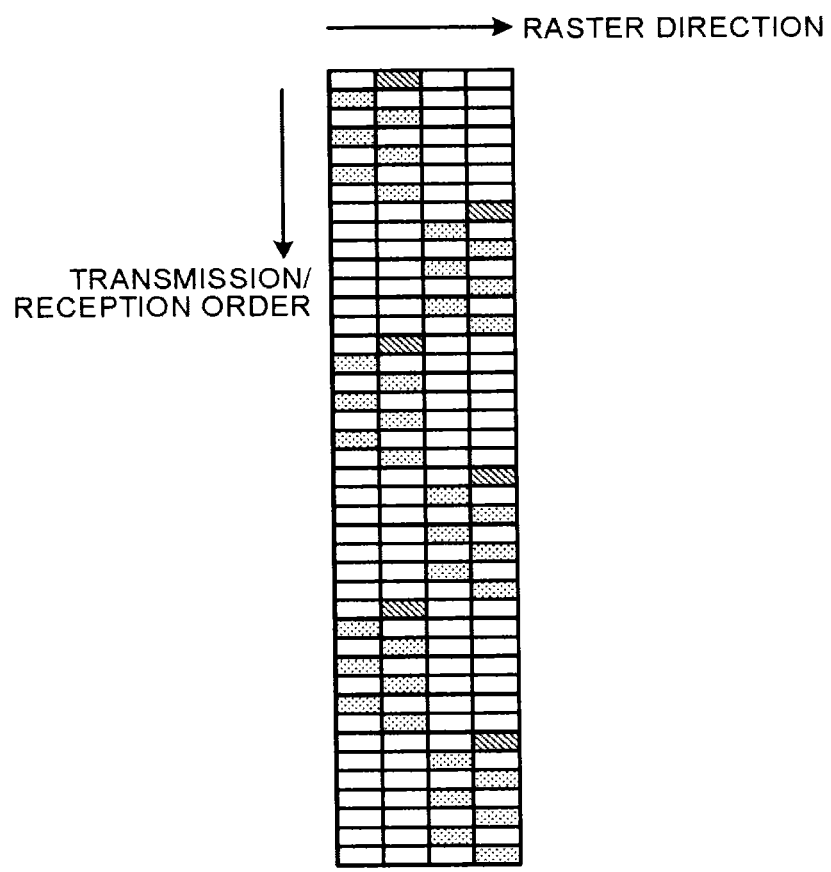
FIG. 2D is a diagram showing one example of irregular interval scan by the control unit according to the first embodiment.

Furthermore, in the example shown in FIG. 2D, it is indicated that the irregular interval scan having a pattern of "-o-o-o----------o-o-o---------o-o-o" is performed in a raster at the left end. Moreover, in the example shown in FIG. 2D, it is indicated that the irregular interval scan having a pattern of "Δ-o-o-o-------Δ-o-o-o-------Δ-o-o-o" is performed in the second raster from left. The pattern of the irregular interval scan by the control unit 18 is not limited to the ones shown in FIG. 2A to FIG. 2D, and is variable.

Figure 3:
FIG. 3 is a diagram showing one example of irregular interval scan in the same raster by the control unit according to the first embodiment.
Figure 3:
Figure 3:
Figure 3:

FIG. 3 is a diagram showing one example of irregular scan in the same raster by the control unit 18 according to the first embodiment. In FIG. 3, the order of reception signals in the identical raster is expressed by numerals for each of the scan patterns shown in FIG. 2A to FIG. 2D. FIG. 3A corresponds to the scan pattern in FIG. 2A, FIG. 3B corresponds to the scan pattern in FIG. 2B, FIG. 3C corresponds to the scan pattern in FIG. 2C, and FIG. 3D corresponds to the scan pattern in FIG. 2D. In the example shown in FIG. 3, dummy data is not shown, and only the reception signals that are used for operation are shown. In other words, FIG. 3 indicates a data string at the identical point in one raster. Moreover, similarly to FIG. 2A to FIG. 2D, a unit time of respective squares is the same, and is, for example, "T".

In the example shown in FIG. 3A, one example of a case of acquiring eight reception signals is indicated. In other words, a case in which data length of one frame of Doppler data (blood flow information) that is used for estimation calculation is eight is indicated. As shown in FIG. 3A, a data interval between the first reception signal and the second reception signal, a data interval between the second reception signal and the third reception signal, a data interval between the sixth reception signal and the seventh reception signal, and a data interval between the seventh reception signal and the eighth reception signal are equal to each other, and are 4T. Meanwhile, a data interval between the third reception signal and the fourth reception signal, a data interval between the fourth reception signal and the fifth reception signal, and a data interval between the fifth reception signal and the sixth reception signal are equal to each other, and are T.

Furthermore, in the example shown in FIG. 3B, another example of the case of acquiring eight reception signals is indicated. As shown in FIG. 3B, a data interval between the first reception signal and the second reception signal, a data interval between the second reception signal and the third reception signal, a data interval between the sixth reception signal and the seventh reception signal, and a data interval between the seventh reception signal and the eighth reception signal are equal to each other, and are 6T. Meanwhile, a data interval between the third reception signal and the fourth reception signal, a data interval between the fourth reception signal and the fifth reception signal, and a data interval between the fifth reception signal and the sixth reception signal are equal to each other, and are 2T.

In the example shown in FIG. 3C, one example of a case of acquiring nine reception signals is indicated. As shown in FIG. 3C, a data interval between the first reception signal and the second reception signal, a data interval between the second reception signal and the third reception signal, a data interval between the fourth reception signal and the fifth reception signal, a data interval between the fifth reception signal and the sixth reception signal, a data interval between the seventh reception signal and the eighth reception signal, and a data interval between the eighth reception signal and the ninth reception signal are equal to each other, and are T. Meanwhile, a data interval between the third reception signal and the fourth reception signal, and a data interval between the sixth reception signal and the seventh reception signal are equal to each other, and are 6T.

In the example shown in FIG. 3D, another example of the case of acquiring nine reception signals is indicated. As shown in FIG. 3D, a data interval between the first reception signal and the second reception signal, a data interval between the second reception signal and the third reception signal, a data interval between the fourth reception signal and the fifth reception signal, a data interval between the fifth reception signal and the sixth reception signal, a data interval between the seventh reception signal and the eighth reception signal, and a data interval between the eighth reception signal and the ninth reception signal are equal to each other, and are 2T. Meanwhile, a data interval between the third reception signal and the fourth reception signal, and a data interval between the sixth reception signal and the seventh reception signal are equal to each other, and are 10T. In the following, a method of applying an eigenvector MTI filter to this irregular interval data string in the Doppler processing unit 14 is explained.

As described, an entire configuration of the ultrasonic diagnostic apparatus according to the first embodiment has been explained. Based on such a configuration, the ultrasonic diagnostic apparatus according to the first embodiment performs CFM by blood flow information (Doppler data) that has been estimated using the MTI filter to an irregular interval data string.

An ultrasonic diagnostic apparatus according to a conventional technique approximates clutter by performing polynomial least-squares fitting on an irregular interval data string, and extracts blood flow information by subtracting this approximation signal from an original signal. In the polynomial least-squares fitting, by calculating a speed by performing autocorrelation operation of a lag 1 between pulse pairs having short data intervals, higher aliasing speed can be obtained while acquiring a signal of longer observation time with a small number of data, and therefore, a cutoff frequency of the MTI filter can be reduced, and even a blood flow at a low flow speed can be extracted separating from a tissue. In addition, because an irregular interval data string is processed at once without dividing into regular intervals, a noise due to a blind frequency does not occur. That is, a blood flow speed of a wide range from a low flow speed to a high flow speed can be displayed without aliasing.

However, in the polynomial least-squares fitting, the filter coefficient is determined in advance, and it has been impossible to avoid occurrence of a motion artifact when movement of a tissue is large. As a method of effectively reducing a motion artifact, although a method of adaptively changing characteristics of an MTI filter (adaptive MTI filter) is effective, a case of applying an adaptive MTI filter to an irregular interval data string has not been known.

Thus, the ultrasonic diagnostic apparatus according to the first embodiment adaptively changes the coefficient of the MTI filter in the color Doppler method in which an irregular interval data string is input, thereby reducing a motion artifact. For example, the ultrasonic diagnostic apparatus according to the first embodiment calculates a correlation matrix using a first data string that is a set of reflected wave data generated based on reflected waves that are generated by transmitting ultrasonic waves without making time intervals of transmission pulses uniform on an identical scan line. Furthermore, the ultrasonic diagnostic apparatus according to the first embodiment calculates a filter coefficient based on a result of principal component analysis using the correlation matrix. Subsequently, the ultrasonic diagnostic apparatus according to the first embodiment extracts a second data string that is included in the first data and that is a set of reflected wave data originated from reflected waves of ultrasonic waves that are reflected on a moving object present on the identical scan line, using the filter coefficient. Moreover, the ultrasonic diagnostic apparatus according to the first embodiment estimates moving object information of the moving object based on the extracted second data string. Subsequently, the ultrasonic diagnostic apparatus according to the first embodiment generates ultrasonic image data based on the moving object information. The ultrasonic diagnostic apparatus according to the first embodiment then displays the ultrasonic image data on the monitor 2. In the following, details of the ultrasonic diagnostic apparatus according to the first embodiment are explained. In the following, blood flow information is explained as one example of the moving object information.

The Doppler processing unit 14 calculates a correlation matrix of an irregular interval data string to acquire an eigenvalue and an eigenvector thereof. By approximating clutter with an eigenvector having a large eigenvalue, and by subtracting from an original signal, a blood flow signal is acquired. Because the eigenvalue and the eigenvector vary according to an input signal, the characteristics of the MTI filter changes according to the input signal. Thus, even large movement of a tissue such as a motion artifact can be suppressed. This method can be considered to approximate clutter by principal component analysis or a technique called Karhunen-Loeve transform. In this technique, energy concentrates in higher eigenvalues. One having large energy in a data string of the color Doppler is clutter. Therefore, a signal approximated by an eigenvector having a large eigenvalue can be regarded as clutter. Because clutter can be separated to be extracted even when movement of a tissue being an origin of clutter in this technique, removal of a motion artifact is enabled.

In the following, details of processing performed by the correlation-matrix calculating unit 141, the filter-matrix calculating unit 142, the MTI-filter processing unit 143 and the estimating unit 144 included in the Doppler processing unit 14 are explained. First, the correlation-matrix calculating unit 141 according to the first embodiment calculates a correlation matrix in a scan range (first scan range) from a data string of reflected wave data at an identical position collected throughout multiple frames by transmission and reception of ultrasonic waves in the scan range (first scan range) formed with multiple scan lines. Specifically, the correlation-matrix calculating unit 141 according to the first embodiment uses a data string of successive reflected wave data at an identical position collected by repeating a scan form in which a scan line is switched each time one ultrasonic wave transmission/reception is performed, throughout the scan range (first scan range), as a data string to calculate a correlation matrix of the scan range. More specifically, the correlation-matrix calculating unit 141 according to the first embodiment uses a data string of successive reflected wave data at an identical position collected by repeating the scan form in which ultrasonic wave transmission/reception is performed once for each scan line in a scan range (first scan range), as a data string to calculate a correlation matrix of the scan range. The correlation-matrix calculating unit 141 according to the first embodiment calculates a correlation matrix using a first data string that is a set of reflected wave data generated based on reflected waves that are generated by transmitting ultrasonic waves without making time intervals of transmission pulses uniform on an identical scan line.

Specifically, the correlation-matrix calculating unit 141 expresses a data string at an identical point in one raster with a column vector x, as indicated in Equation (1). In other words, the column vector "x" indicates a data string at one scan position. This column vector x includes elements $x_1, x_2, \ldots x_L$ are included. A numeral subscript to each element corresponds to a numeral in a square shown in FIG. 3. For example, in a case of FIG. 3A, L=8. "L" indicates length of a column vector "$X_m$", and is data length that is used for estimation calculation of Doppler data (blood flow information) of one frame.

$$x = \begin{pmatrix} x_1 \\ x_2 \\ \vdots \\ x_L \end{pmatrix} \quad (1)$$

Subsequently, the correlation-matrix calculating unit 141 calculates a correlation matrix "$R_{xx}$" by Equation (2) below. That is, the correlation-matrix calculating unit 141 takes an ensemble average by signal averaging a data string at spatially different position based in Equation (2). In other words, the correlation-matrix calculating unit 141 calculates an autocorrelation matrix of a data string at each of multiple sample points by Equation (2), and calculates an average of the autocorrelation matrix of each of the sample points. A subscript m of $x_m$ expresses a position in a space, and the total number of the positions m is M. The position "m" is expressed by a two-dimensional coordinate system in a case of two-dimensional scan, and is expressed by a three-dimensional coordinate system in a case of three-dimensional scan. H expresses a transposition (Hermitian transposition) of a matrix in which each element of a matrix is complex conjugated. A correlation matrix "$R_{xx}$" is to be a matrix with L lines and L columns. As described above, the data length "L" of a data string for which a correlation matrix is calculated can be arbitrarily changed.

The correlation-matrix calculating unit 141 may calculate one covariance matrix using data of an entire scan range in color Doppler, or may calculate a covariance matrix for each of blocks obtained by dividing the scan range, as data at a spatially different position.

$$R_{xx} = \frac{1}{M} \sum_{m=1}^{M} x_m x_m^H \quad (2)$$

Subsequently, the filter-matrix calculating unit 142 calculates a filter coefficient based on a result of principal component analysis using the correlation matrix. In other words, the filter-matrix calculating unit 142 performs principal component analysis using the correlation matrix, and calculates a filter coefficient to suppress clutter from a tissue by performing matrix operation to approximate and reduce a clutter component as a principal component. For example, the filter-matrix calculating unit 142 calculates an eigenvalue and an eigenvector of the matrix $R_{xx}$ with L lines and L columns. A matrix in which eigenvectors are aligned from left in descending order of eigenvalue is V. When signals are approximated with the top K pieces of principal components, an equation as indicated below is obtained. Equation (3) indicates a case in which a matrix at the center is a diagonal matrix, and as for diagonal elements, K pieces from top left are 1 and the rest is 0. "$V^H$" in Equation (3) is a complex conjugate transposition matrix of "V". In the right side of Equation (3), a matrix between "V" and "$V^H$" is a diagonal matrix with L lines and L columns.

$$V \begin{pmatrix} 1 & & & & & \\ & 1 & & & & \\ & & \ddots & & & \\ & & & 1 & & \\ & & & & 0 & \\ & & & & & 0 \end{pmatrix} V^H x \quad (3)$$

When Equation (3) is subtracted from an original signal, Equation (4) is acquired. I expresses a unit matrix. That is, when an input data string x is multiplied by a matrix W expressed in Equation (5), an MTI filter can be structured. An MTI filter matrix "W" is to be a matrix with L lines and L columns based on Equation (5).

$$x - V \begin{pmatrix} 1 & & & \\ & 1 & & \\ & & \ddots & \\ & & & 0 \\ & & & & 0 \end{pmatrix} V^H x = \left\{ I - V \begin{pmatrix} 1 & & & \\ & 1 & & \\ & & \ddots & \\ & & & 0 \\ & & & & 0 \end{pmatrix} V^H \right\} x = \quad (4)$$

$$\left\{ V V^H - V \begin{pmatrix} 1 & & & \\ & 1 & & \\ & & \ddots & \\ & & & 0 \\ & & & & 0 \end{pmatrix} V^H \right\} x = V \begin{pmatrix} 0 & & & \\ & 0 & & \\ & & \ddots & \\ & & & 1 \\ & & & & 1 \end{pmatrix} V^H x$$

$$W = V \begin{pmatrix} 0 & & & \\ & 0 & & \\ & & \ddots & \\ & & & 1 \\ & & & & 1 \end{pmatrix} V^H \quad (5)$$

In the diagonal matrix in the right side of Equation (5), the number of 0s is K. This is a process to reduce a rank of the matrix, and K is referred to as a rank cut value. Even if the rank cut value K is fixed, the eigenvalue thereof increases when a tissue moves, and therefore, a motion artifact is removed as much as possible using the rank cut value. However, when movement of the tissue is large, the value of the eigenvector becomes large corresponding to the movement of the tissue. Therefore, it is preferable that the rank cut value be large. The rank cut value may be changed by an operator using a switch and the like in the apparatus, but a method of changing the rank cut value adaptively from the magnitude of an eigenvalue is suitable.

For example, the filter-matrix calculating unit 142 determines the number of principal components to be reduced, that is, a value of the rank cut value, by a predetermined value or a value specified by an operator. However, when a tissue the movement speed of which varies with time by pulsation, such as a heart and a blood vessel, is included in a scan range, the value of the rank cut value is preferable to be determined adaptively based on the magnitude of the eigenvalue. That is, the filter-matrix calculating unit 142 changes the number of principal components to be reduced according to the magnitude of the eigenvalue of a correlation matrix. In the present embodiment, the filter-matrix calculating unit 142 changes the number of ranks to be reduced according to the magnitude of an eigenvalue.

Figures 4, 5:
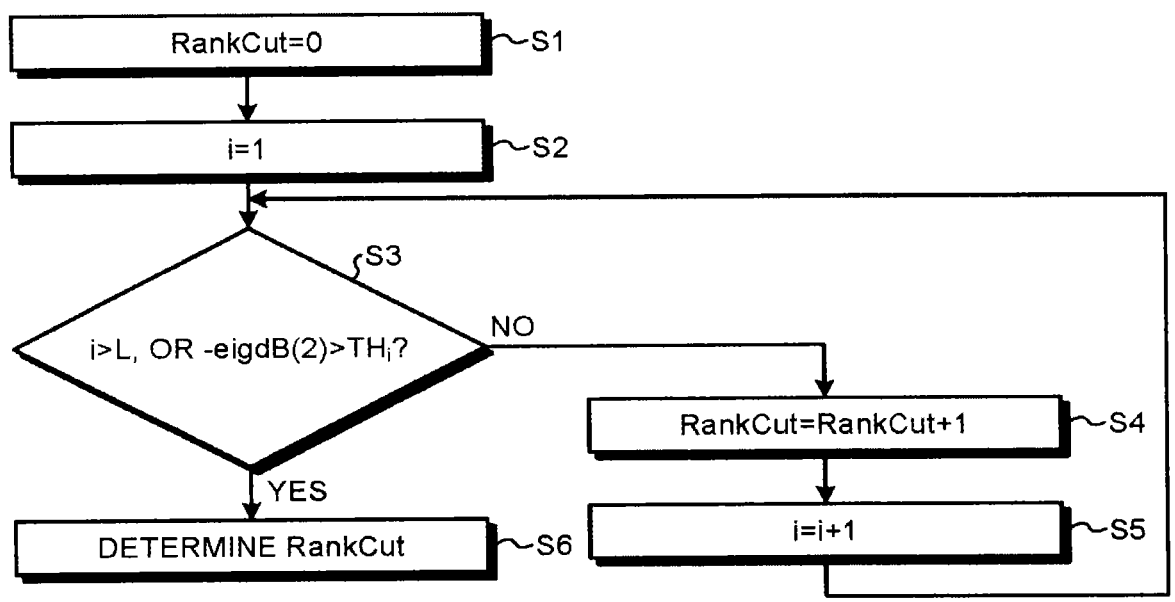
FIG. 4 is a diagram for explaining one example of determination processing of a rank cut value according to the first embodiment.
FIG. 5 is a diagram for explaining one example of determination processing of the rank cut value according to the first embodiment.

The logic to determine the rank cut value adaptively based on the magnitude of an eigenvalue is required to be optimized according to a part at which ultrasonic scan is performed. For example, the filter-matrix calculating unit 142 determines the rank cut value based on a threshold shown in FIG. 4 and an algorithm shown in FIG. 5. The algorithm shown in FIG. 5 is an algorithm to determine the rank cut value based on a value obtained by dividing the second largest eigenvalue by the largest eigenvalue. FIG. 4 and FIG. 5 are diagrams for explaining one example of determination processing of the rank cut value according to the first embodiment.

First, the filter-matrix calculating unit 142 defines the k-th eigenvalue as "eig(k)" in the alignment in which eigenvalues of the correlation matrix "$R_{xx}$" are aligned in descending order. "k" is a positive integer of "$1 \leq k \leq L$". The filter-matrix calculating unit 142 calculates a value "eigdB(k)" expressing a value obtained by dividing the k-th largest eigenvalue by the largest eigenvalue "eig(1)" by a unit of decibel (dB) by Equation (6) below.

$$eigdB(k) = 10 * \log_{10}(abs(eig(k))/abs(eig(1))) \quad (6)$$

In Equation (6), "abs" is a function to calculate an absolute value. In Equation (6), "eigdB(2)" where "k=2" is a value expressing a value that is obtained by dividing the second largest eigenvalue by the largest eigenvalue "eig(1)" by the unit of dB.

Moreover, the filter-matrix calculating unit 142 uses L pieces of thresholds ($TH_i$ where $1 \leq i \leq L$) to determine the rank cut value because L pieces of eigenvalues are obtained. A value that varies according to a value of i is set to $TH_i$. For example, when "L=8", eight pieces of thresholds "$TH_1$ to $TH_8$" are set as shown in FIG. 4. In FIG. 4, $TH_1$ and $TH_2$ are set to "1000000 dB". Furthermore, in FIG. 4, $TH_3$ is set to "20 dB", and $TH_4$ is set to "15 dB". Furthermore, in FIG. 4, $TH_5$ is set to "10 dB", and $TH_6$ is set to "5 dB". Moreover, in FIG. 4, $TH_7$ and $TH_8$ are set to "−1 dB". When the thresholds exemplified in FIG. 4 are used, the rank cut value is to be a value equal to or larger than 2 and equal to or smaller than 6 based on the algorithm in FIG. 5 explained below. In FIG. 5, the rank cut value is indicated as "RankCut".

First, the filter-matrix calculating unit 142 sets "RankCut=0" (step S1), and sets "i=1" (step S2). The filter-matrix calculating unit 142 then determines whether "i" is larger than "L", or whether "−eigdB(2)" is larger than "$TH_i$" (step S3). When "i" is equal to or smaller than "L", and "−eigdB(2)" is equal to or smaller than "$TH_i$" (step S3, NO), the filter-matrix calculating unit 142 increments the rank cut value as "RankCut=RankCut+1" (step S4).

Subsequently, the filter-matrix calculating unit 142 sets "i=i+1" (step S5), and performs determination processing at step S3. "−eigdB(2)" that is used for the determination processing at step S3 after the processing after first step S5 is, for example, a value that is obtained by multiplying, by "−1", a value expressing a value obtained by dividing the second largest eigenvalue by the largest eigenvalue "eig(1)" by the unit of dB, in an alignment from which the largest eigenvalue is removed from an alignment in which L pieces of eigenvalues are aligned in descending order.

On the other hand, when "i" is larger than "L", or when "−eigdB(2)" is larger than "$TH_i$" (step S3, YES), the filter-matrix calculating unit 142 determines the latest "RankCut" as the number of ranks to be reduced (step S6). For example, the filter-matrix calculating unit 142 determines the rank cut value to 4 when eigdB(2)=−12 dB under the condition shown in FIG. 4.

The algorithm to determine the rank cut value adaptively based on the magnitude of an eigenvalue can be achieved by various algorithms other than the algorithm described above. For example, these algorithms can be selected according to a part to be imaged.

The filter-matrix calculating unit 142 determines the rank cut value for each display frame by the algorithm exemplified in FIG. 5, and calculates the MTI filter matrix "W".

Subsequently, the MTI-filter processing unit 143 extracts a second data string that is included in the first data string and that is a set of reflected wave data originated from reflected waves of ultrasonic waves that are reflected on a moving object present on an identical scan line, using the filter coefficient. In other words, the MTI-filter processing unit 143 outputs a data string in which a clutter component is suppressed and a blood flow signal derived from a blood flow is extracted, from a data string of successive reflected wave data of an identical position (identical sample point) using the filter coefficient. In the present embodiment, the MTI-filter processing unit 143 uses a filter matrix to output a data string in which a clutter component is suppressed and a blood flow signal derived from a blood flow is extracted, from a data string of successive reflected wave data of an identical position (identical sample point). Specifically, the MTI-filter processing unit 143 calculates a column vector "$y_m$" to be output data of a position "m" from the input data and the MTI filter matrix "W" when a column vector "$x_m$" at the position "m" is input data, by Equation (7) below. Length of the column vector "$y_m$" is "L".

$$y_m = W x_m \quad (7)$$

The MTI-filter processing unit 143 performs calculation of Equation (7) for each of "M" sample points. The MTI-filter processing unit 143 thereby outputs output data of each of the "M" sample points to the estimating unit 144.

The estimating unit 144 estimates moving object information of a moving object based on the data string of extracted signals from the moving object. For example, the estimating unit 144 estimates blood flow information of the position "m" by performing autocorrelation operation and speed/dispersion/power estimation processing from the column vector "$y_m$" being output data of the position "m". First, the estimating unit 144 performs operation of an autocorrelation value of lag 0 and lag 1 from the column vector "$y_m$". When lag 0 is "$C_0$" and lag 1 is "$C_1$", the estimating unit 144 calculates lag 0 "$C_0$" by Equation (8) below.

$$c_0 = \frac{1}{L} \sum_{i=1}^{L} |y_i|^2 \quad (8)$$

Moreover, the estimating unit 144 uses the shortest pulse pair in an irregular interval data string for calculation of lag 1 "$C_1$". For example, in the case shown in FIG. 3A, a data interval between the third reception signal and the fourth reception signal, a data interval between the fourth reception signal and the fifth reception signal, and a data interval between the fifth reception signal and the sixth reception signal are T and those are the shortest pulse pairs. In such a case, the estimating unit 144 calculates lag 1 by Equation (9) below.

$$c_1 = \frac{1}{3} \sum_{i=3,4,5} y_i^* y_{i+1} \qquad (9)$$

Furthermore, in the case shown in FIG. 3B, because the shortest pulse pairs are the same as the shortest pulse pairs of FIG. 3A, Equation (9) same as the above is used. The accuracy of speed decreases at an end portion of a short pulse pair due to the characteristics of the MTI filter. Therefore, the estimating unit 144 may decrease the influence of the MTI filter by using only one pulse pair that is i=4 in Equation (9). In such a case, the stability by addition is degraded.

Moreover, for example, in the case shown in FIG. 3C, a data interval between the first reception signal and the second reception signal, a data interval between the second reception signal and the third reception signal, a data interval between the fourth reception signal and the fifth reception signal, a data interval between the fifth reception signal and the sixth reception signal, a data interval between the seventh reception signal and the eighth reception signal, and a data interval between the eighth reception signal and the ninth reception signal are T and those are the shortest pulse pairs. In such a case, the estimating unit 144 calculates lag 1 by Equation (10) below.

$$c_1 = \frac{1}{6} \sum_{i=1,2,4,5,7,8} y_i^* y_{i+1} \qquad (10)$$

Similarly, because the shortest pulse pairs of FIG. 3D are the same as the shortest pulse pairs of FIG. 3C, the estimating unit 144 uses Equation (10) same as the above. The estimating unit 144 may decrease the influence of the MTI filter by using two pulse pairs that are i=4, 5 in Equation (10).

In Equation (8) to Equation (10), the subscript "m" indication the position of the column vector "$y_m$" is omitted, and instead, an element of column vector "$y_m$" is expressed by a subscript "i". Moreover, in Equation (9) and Equation (10), the superscript asterisk "*" indicates complex conjugation. The estimating unit 144 calculates "$C_0$" and "$C_1$" of each of the "M" sample points.

The estimating unit 144 then calculates the speed "V" from "$C_0$" and "$C_1$" by Equation (11) below. The estimating unit 144 calculates the speed of the moving object from a pulse pair having short intervals in the second data string, as moving object information.

$$V = a\tan2(imag(c_1), real(c_1)) \qquad (11)$$

Furthermore, the estimating unit 144 calculates a dispersion "T" from "$C_0$" and "$C_1$" by Equation (12) below, and calculates a power "P" from "$C_0$" by Equation (13) below. The estimating unit 144 may calculate the power of a moving object using at least a part of a data string of signals from the moving object, as moving object information.

$$T = 1 - \frac{|c_1|}{c_0} \qquad (12)$$

$$P = 10\log_{10}(c_0) \qquad (13)$$

"atan2" in Equation (11) is an "arctangent function" to output an angle "$-\pi$ to $+\pi$", and "imag" is a function to output only an imaginary part from a complex number, and "real" is a function to output only a real part from a complex number. The power is acquired as lag 0 by autocorrelation operation, and the speed and the dispersion are acquired by frequency analyzing a result of the autocorrelation operation. The speed acquired by Equation (11) is expressed by an angle from $-\pi$ to $+\pi$, and to convert this into a speed V' in a unit of millisecond (m/s), Equation (14) is acquired where the interval of the shortest pulse pairs of an irregular interval data string is T. Moreover, C is a sonic speed of an ultrasonic wave in a living body, and $f_0$ is a center frequency of an ultrasonic wave. An aliasing speed V'$_{max}$ is expressed as Equation (15).

$$V' = \frac{C}{4\pi f_0 T} \qquad (14)$$

$$V'_{max} = \frac{C}{4\pi f_0 T} \qquad (15)$$

For example, if all of data intervals are the data interval between the first and the second data, the cycle is 4T. In such a case, the aliasing speed is to be ¼ based on Equation (15). By inserting data having the cycle T as the data interval between the third and the fourth data, the data interval between the fourth and the fifth data, and the data interval between the fifth and the sixth data shown in FIG. 3A, the aliasing speed can be improved to four times as much as the cycle 4T.

Furthermore, to maintain the data length of FIG. 3A with the data interval T as it is, 23 pieces of data corresponding to the number of squares indicated in FIG. 3A are required. Because the actual number of data of FIG. 3A is 8, it is possible to reduce the number of data to ½.₈₇₅ at the same observation time. As described, to reduce the number of data contributes to improvement of the frame rate.

Moreover, as the observation time becomes longer, an MTI filter having an abrupt knee characteristic can be configured when the horizontal axis is the speed m/s. That is, clutter can be suppressed. In other words, for example, by performing a scan of an irregular interval data string as the one in FIG. 2A, three contradictory demands of a high frame rate, high flow speed detection, and low flow speed detection can be satisfied.

The estimating unit 144 calculates "V, T, P" of each of the "M" sample points. The estimating unit 144 then outputs "V, T, P" of each of the "M" sample points to the image generating unit 15 as one frame of Doppler data.

The image generating unit 15 generates ultrasonic image data based on the moving object information. In other words, the image generating unit 15 generates ultrasonic image data (color Doppler image data) from blood flow information (Doppler data) estimated using the filter coefficient. In the present embodiment, the image generating unit 15 generates ultrasonic image data (color Doppler image data) from blood flow information (Doppler data) that is estimated using the MTI filter matrix. The control unit 18 causes a monitor 2 to display the ultrasonic image data (color Doppler image data).

Figure 6:
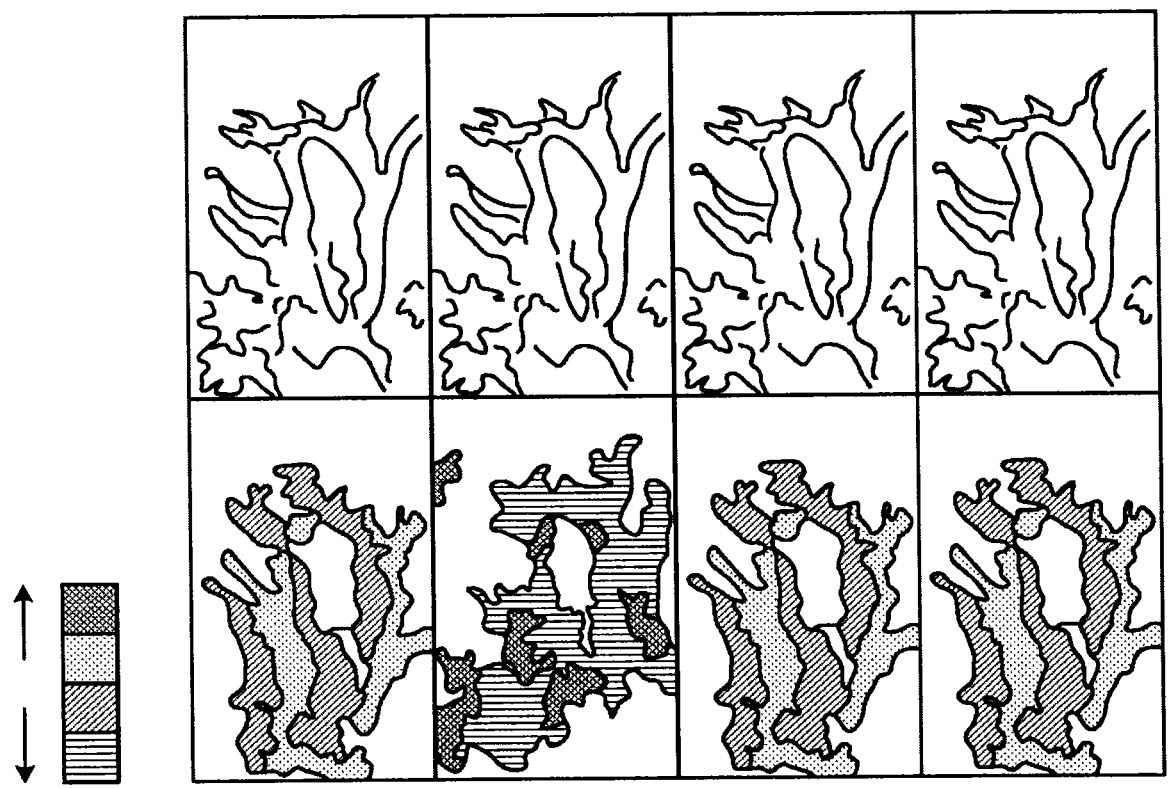
FIG. 6 is a diagram showing one example of ultrasonic image data according to the first embodiment.
Figure 7:
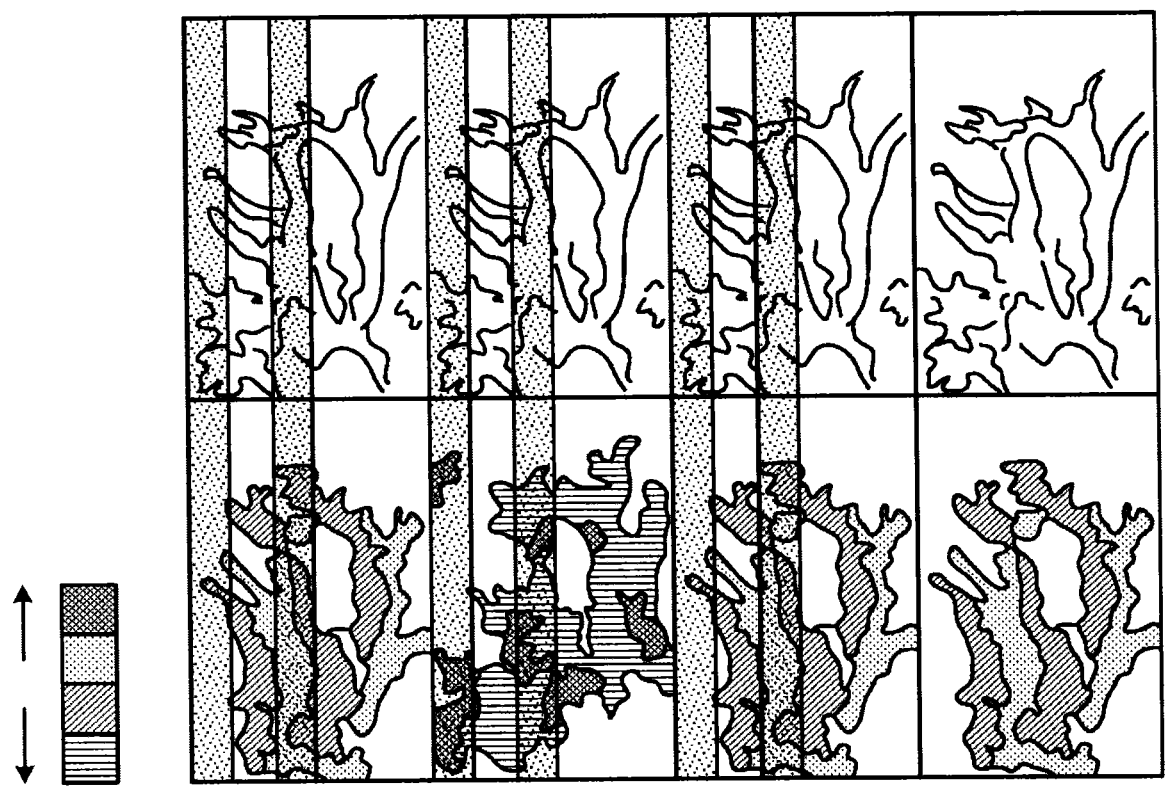
FIG. 7 is a diagram showing one example of ultrasonic image data according to the first embodiment.

FIG. 6 and FIG. 7 are diagrams showing one example of ultrasonic image data according to the first embodiment. In FIG. 6 and FIG. 7, an example of a kidney blood flow is shown. Moreover, in FIG. 6, an image when movement of a kidney is small is shown, and in FIG. 7, an image when movement of a kidney is large is shown.

In FIG. 6 and FIG. 7, a power image is shown in the upper row, and a speed image is shown in the lower row. Furthermore, the left column, "original data", "thinned-out data", "polynomial fitting data", and "eigenvector data" are shown in this order. The "original data" is a regular interval data string with 32 pieces of data. The "thinned-out data" is an image computed using 8 pieces of data by thinning out a data string of 32 pieces of data at regular intervals every 4 pieces of data.

The "polynomial fitting data" is an image that is obtained by approximating an irregular interval data string with a cubic polynomial, to subtract from an original signal. The "eigenvector data" is an image in which an irregular interval data string having data length of 8 is processed by the eigenvector MTI filter according to the first embodiment. In the "polynomial fitting data" and "eigenvector data", an irregular interval data string that is thinned out leaving only a central portion dense, and that has the data length of 8 and the scan pattern shown in FIG. 3A is used. The rank cut value of the eigenvector MTI filter is fixed to four.

As shown in FIG. 6, in the speed image of the "original data", branches of blood vessels according to directions of blood flows are displayed. The blood flow direction and the speed in the speed image are indicated by scales. On the other hand, in the "thinned-out data", because the aliasing speed is ¼ of the "original data", aliasing occurs in the speed image. Therefore, the directions of blood flows cannot be reproduced accurately, and branches of the blood vessels are not displayed.

Moreover, the speed images of the "polynomial fitting data" and the "eigenvector data" are substantially equivalent, and are images with significantly smaller aliasing compared to the speed image of the "thinned-out data". Furthermore, as for the speed images of the "polynomial fitting data" and the "eigenvector data", images quite close to the speed image of the "original data" are displayed.

Moreover, as shown in FIG. 7, in the power images of the "original data", the "thinned-out data", and the "polynomial fitting data", motion artifacts are mixed in some blocks. On the other hand, in the power image of the "eigenvector data", a motion artifact is not mixed, and a highly precise blood flow image is displayed. Similarly, in the speed images of the "original data", the "thinned-out data", and the "polynomial fitting data" also, motion artifacts are mixed in some blocks, while a motion artifact is not mixed in the speed image of the "eigenvector data". Furthermore, similarly to when movement is small, the speed image of the "eigenvector data" has significantly smaller aliasing compared to the speed image of the "thinned-out data".

Figure 8:
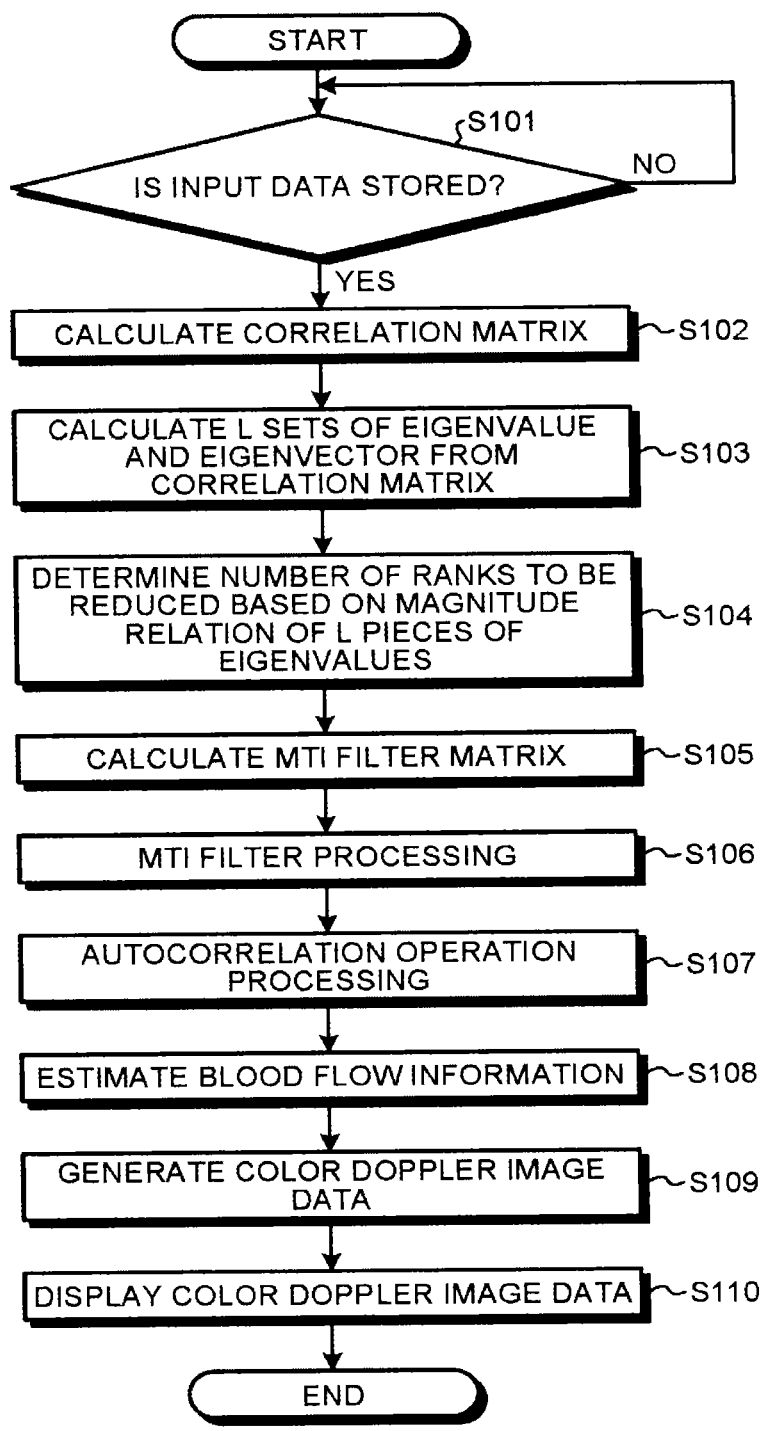
FIG. 8 is a flowchart for explaining one example of processing performed by the ultrasonic diagnostic apparatus according to the first embodiment.

Next, one example of processing performed by the ultrasonic diagnostic apparatus according to the first embodiment is explained using FIG. 8. FIG. 8 is a flowchart for explaining one example of the processing performed by the ultrasonic diagnostic apparatus according to the first embodiment. The flowchart exemplified in FIG. 8 is a flowchart explaining generation/display processing of Doppler image data that is performed by the ultrasonic diagnostic apparatus according to the first embodiment.

As shown in FIG. 8, the control unit 18 of the ultrasonic diagnostic apparatus according to the first embodiment determines whether one frame of an irregular interval data string is input (step S101). When determining that one frame of the irregular interval data string is input (step S101: YES), the control unit 18 proceeds to step S102. On the other hand, when not determining that one frame of the irregular interval data string is input (step S101: NO), the control unit 18 repeats step S101.

Subsequently, the correlation-matrix calculating unit 141 calculates a correlation matrix of a scan range (step S102), and the filter-matrix calculating unit 142 calculates L sets of an eigenvalue and an eigenvector from the correlation matrix (step S103).

The filter-matrix calculating unit 142 then determines the number of ranks to be reduced, based on the magnitude relation of the L pieces of eigenvalues (step S104), and calculates the MTI filter matrix (step S105). The MTI-filter processing unit 143 performs MTI filter processing (step S106), and the estimating unit 144 performs autocorrelation operation processing using output data that is output by the MTI filter processing (step S107). The estimating unit 144 estimates blood flow information from a result of the autocorrelation operation processing (step S108).

The image generating unit 15 generates color Doppler image data from the blood flow information (step S109), and the monitor 2 displays the color Doppler image data, controlled by the control unit 18 (step S110), and the processing is ended.

As described above, in the first embodiment, the estimation processing of blood flow information using the eigenvector MTI filter is performed in combination with a high-frame-rate ultrasonic scan by an irregular-interval-data string scan. Thus, in the first embodiment, by calculating one correlation matrix for an entire scan range, and the same eigenvector MTI filter can be applied to an entire image. This enables to provide an image in which a motion artifact is significantly reduced by an adaptive MTI filter using an eigenvector for an irregular interval data string in the first embodiment. Furthermore, by calculating a speed from an autocorrelation function of lag 1 of a pulse pair having the shortest data interval in an irregular interval data string, a speed having high aliasing speed can be displayed.

Moreover, by using an irregular interval data string, an MTI filter having an abrupt knee characteristic can be configured with a low cutoff frequency with small number of data. That is, a system that is capable of detecting even a low flow speed (=an MTI filter having an abrupt knee characteristic with a low cutoff frequency) with a high frame rate (=the small number of data) can be achieved.

Furthermore, in the first embodiment, by using an eigenvector MTI filter that is calculated by the rank cut value determined adaptively according to the magnitude of an eigenvalue, the characteristics of the MTI filter can be changed according to movement of a tissue. As a result, in the first embodiment, a motion artifact can be further significantly suppressed.

Second Embodiment

Although one correlation matrix is calculated in one frame in the first embodiment, processing may be performed by dividing into regions, and by calculating a correlation matrix for each region to calculate calculating an MTI filter matrix. Therefore, in the second embodiment, a method of further improving the image quality of Doppler image data using an eigenvector MTI filter with processing by dividing into regions, and by calculating a correlation matrix for each region to calculate calculating an MTI filter matrix is explained.

An ultrasonic diagnostic apparatus according to the second embodiment has a similar configuration as the ultrasonic diagnostic apparatus according to the first embodiment explained using FIG. 1. However, the Doppler processing unit 14 according to the second embodiment calculates an MTI filter matrix by processing explained below.

In the first embodiment, one correlation matrix is calculated for an entire scan range to display a blood flow, and the same MTI filter is applied to an entire image. On the other hand, when movement of a tissue is large depending on a position in a scan range to display a blood flow, it is desirable that an optimal MTI filter be applied to each processing block by dividing the scan range into multiple processing blocks and by calculating an eigenvector MTI filter for each of the processing blocks. However, in such a case, a discontinuous boundary occurs between processing blocks in Doppler image data due to characteristic differences of the filters.

Therefore, in the second embodiment, a coefficient of an eigenvector MTI filter is calculated by spatially interpolating the correlation matrix calculated for each processing block.

First, the correlation-matrix calculating unit 141 according to the second embodiment calculates a correlation matrix for each of multiple regions (multiple processing blocks) obtained by dividing a scan range in which transmission and reception of ultrasonic waves are performed. The correlation-matrix calculating unit 141 then calculates a correlation matrix of each of multiple subdivision ranges (multiple subdivision processing blocks) that are obtained by further dividing each of the processing blocks, by interpolation processing using the correlation matrix of each of the processing blocks.

The filter-matrix calculating unit 142 according to the second embodiment calculates a filter coefficient of each subdivision processing block from the correlation matrix of each of the subdivision processing blocks. Specifically, the filter-matrix calculating unit 142 calculates a filter matrix of each of the subdivision processing blocks from the correlation matrix of each of the subdivision processing blocks. Subsequently, the MTI-filter processing unit 143 according to the second embodiment extracts a blood flow signal of each sample point using the filter coefficient of each of the subdivision processing blocks. Specifically, the MTI-filter processing unit 143 extracts a blood flow signal of each sample point using the filter matrix of each of the subdivision processing blocks. Subsequently, the estimating unit 144 according to the second embodiment estimates moving object information based on a data string of signals from a moving object in each of the subdivision processing blocks. For example, the estimating unit 144 according to the second embodiment estimates blood flow information of each sample point. Thus, the image generating unit 15 generates ultrasonic image data (Doppler image data) from the blood flow information estimated using the filter coefficient of each of the subdivision processing blocks. Specifically, the image generating unit 15 generates ultrasonic image data (Doppler image data) from blood flow information estimated using the filter matrix of each of the subdivision processing blocks.

Figure 9:
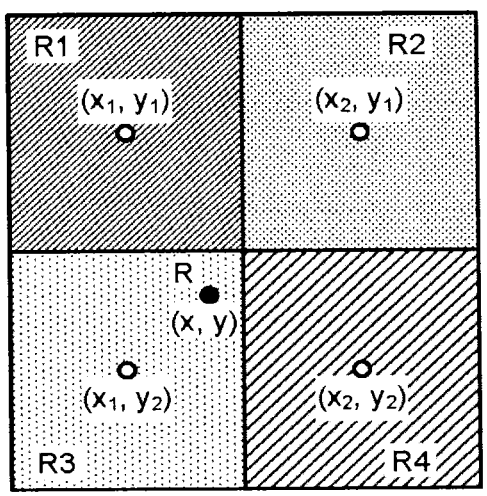
FIG. 9 is a diagram showing one example of processing performed by a correlation-matrix calculating unit according to a second embodiment.

FIG. 9 is a diagram showing one example of processing performed by the correlation-matrix calculating unit according to the second embodiment. For example, a scan range is divided into four processing blocks (R1, R2, R3, R4) as exemplified in FIG. 9. The number of division of a scan range or the respective processing blocks can be arbitrarily set. The correlation-matrix calculating unit 141 performs calculation processing using Equation (2) explained in the first embodiment for each of the processing blocks R1 to R4. Thus, the correlation-matrix calculating unit 141 calculates a correlation matrix "$R_1$" of the processing block R1, a correlation matrix "$R_2$" of the processing block R2, a correlation matrix "$R_3$" of the processing block R3, and a correlation matrix "$R_4$" of the processing block R4. As shown in FIG. 9, center coordinates of the processing block R1 is "$x_1, y_1$), center coordinates of the processing block R2 is "$x_2, y_1$), center coordinates of the processing block R3 is "$x_1, y_2$), and center coordinates of the processing block R4 is "$x_2, Y_2$).

For example, the correlation-matrix calculating unit 141 calculates a correlation matrix of the sample point R(x, y) by bilinear interpolation using Equation (16) below when the subdivision processing blocks are set as individual sample points in the scan range.

$$R = \frac{R_1(x_2 - x)(y_2 - y) + R_2(x - x_1)(y_2 - y) + R_3(x_2 - x)(y - y_1) + R_4(x - x_1)(y - y_1)}{(x_2 - x_1)(y_2 - y_1)} \quad (16)$$

Subsequently, the filter-matrix calculating unit 142 calculates an MTI filter matrix of each of the M sample points using the correlation matrix of each of the M sample points by Equation (5). The filter-matrix calculating unit 142 determines the rank cut value for each of the M sample points according to the magnitude of an eigenvalue. The MTI-filter processing unit 143 then extracts a blood flow signal of each sample point using a corresponding MTI filter matrix, and the estimating unit 144 estimates blood flow information of each sample point.

Figure 10:
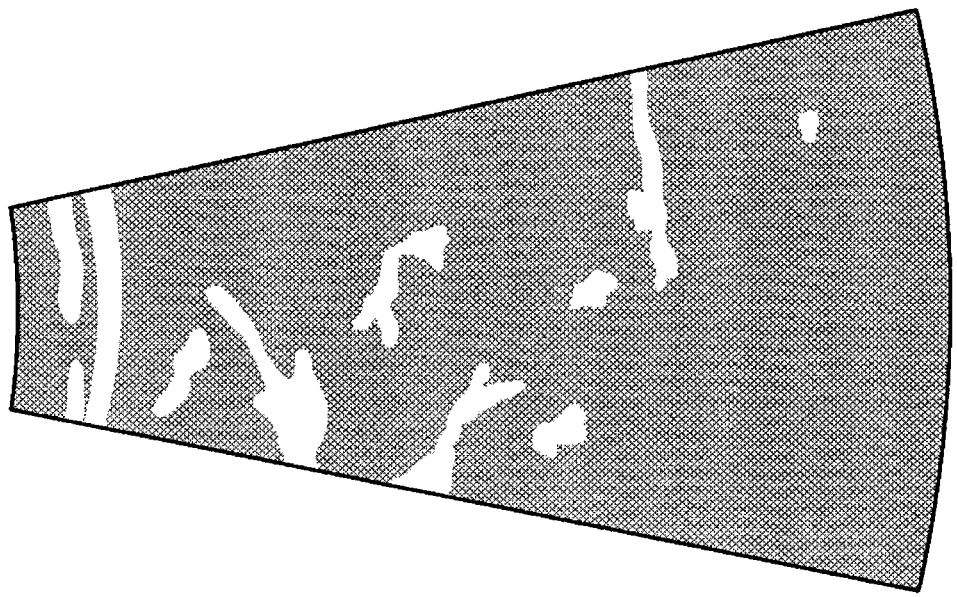
FIG. 10 is a diagram for explaining an effect of the second embodiment.
Figure 10:
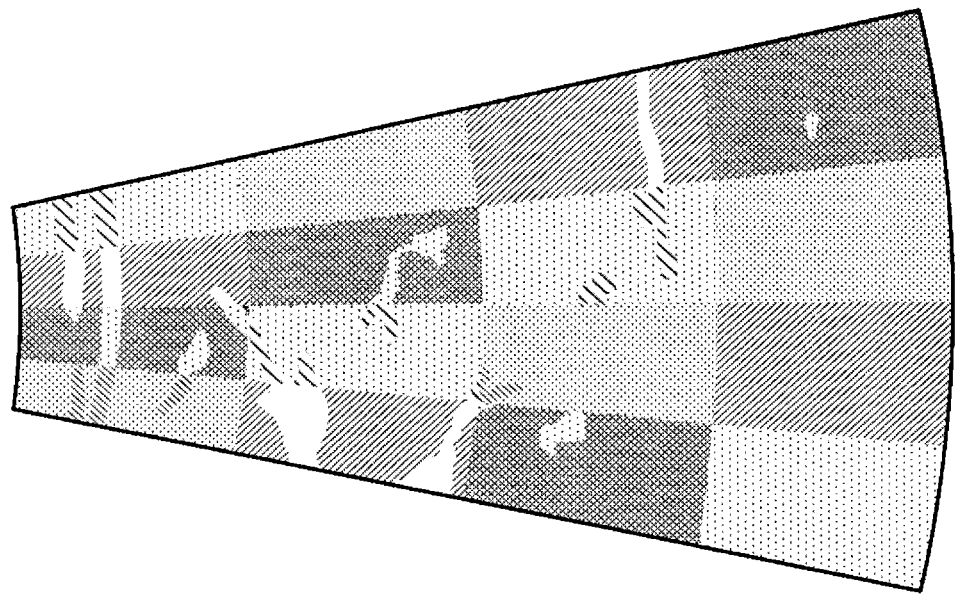

FIG. 10 is a diagram for explaining an effect of the second embodiment. A drawing on the left in FIG. 10 is Doppler image data that is displayed when a scan range in which blood flow display is performed is divided into 16 processing blocks and an MTI filter matrix is calculated in each of the processing blocks. On the other hand, a drawing on the right in FIG. 10 is Doppler image data that is displayed when a scan range in which blood flow display is performed is divided into 16 processing blocks, a correlation matrix of each of sample points is calculated by interpolation processing, and an MTI filter matrix is calculated in each of the sample points.

As exemplified in the drawing on the left in FIG. 10, in the Doppler image data "without interpolation" for which the interpolation processing described above is not performed, discontinuous boundaries are created among the 16 processing blocks. On the other hand, as exemplified in the drawing on the right in FIG. 10, in the Doppler image data "with interpolation" for which the interpolation processing described above is performed, a discontinuous boundary is not created among the 16 processing blocks.

The case in which a subdivision processing block is formed with one sample point has been explained above. However, in the second embodiment, to reduce the processing load, an MTI filter matrix may be calculated in each of subdivision processing blocks obtained by dividing a scan range with, for example, 10 sample points.

Figure 11:
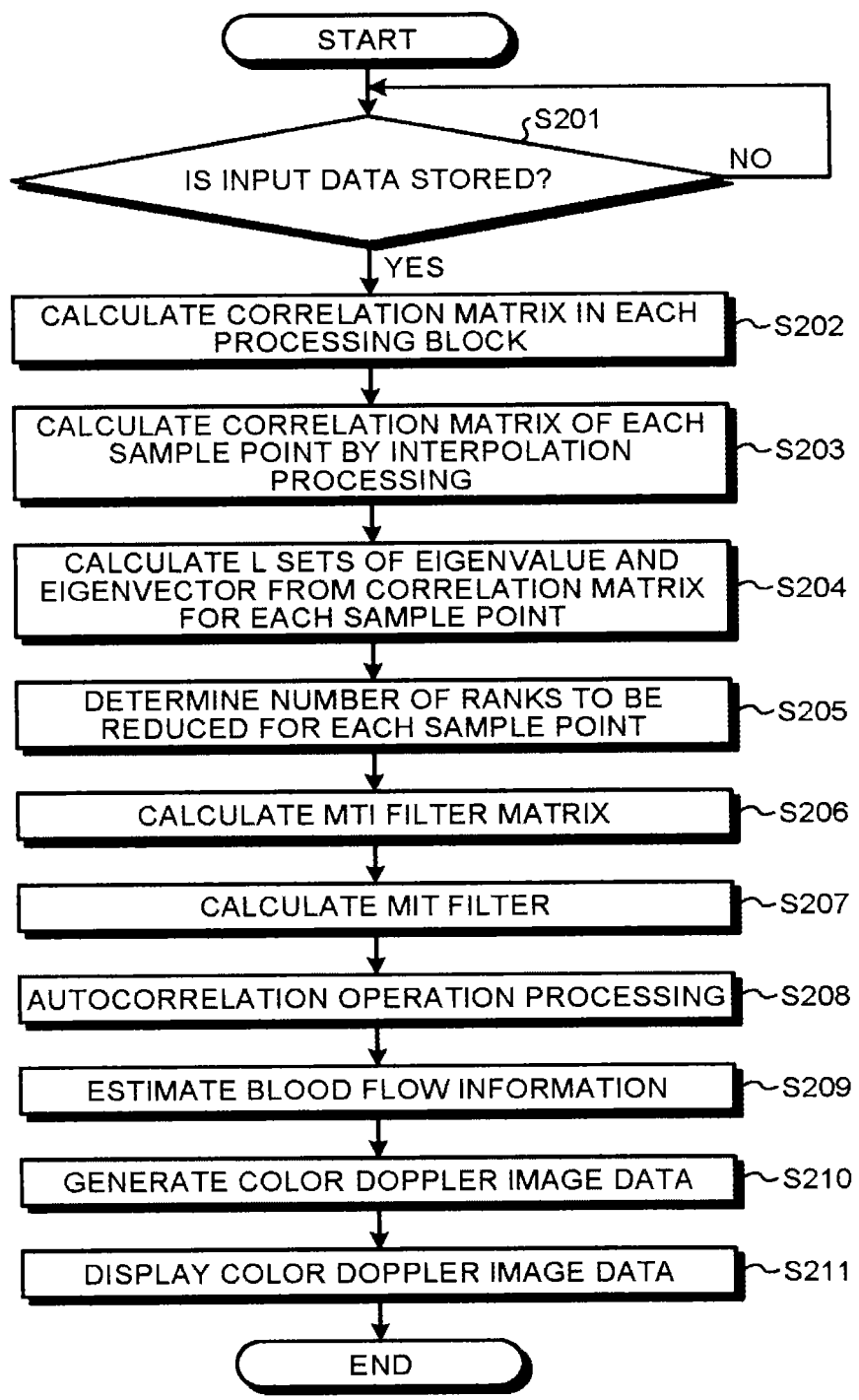
FIG. 11 is a flowchart for explaining one example of processing performed by the ultrasonic diagnostic apparatus according to the second embodiment.

Next, an example of processing performed by the ultrasonic diagnostic apparatus according to the second embodiment is explained using FIG. 11. FIG. 11 is a flowchart for explaining one example of processing performed by the ultrasonic diagnostic apparatus according to the second embodiment. The flowchart exemplified in FIG. 11 is a flowchart explaining generation/display processing of Doppler image data performed by the ultrasonic diagnostic apparatus according to the second embodiment. In FIG. 11, a case in which a subdivision processing block is set as one sample point is exemplified.

As shown in FIG. 11, the control unit 18 of the ultrasonic diagnostic apparatus according to the second embodiment determines whether one frame of an irregular interval data string is input (step S201). When determining that one frame of the irregular interval data string is input (step S201: YES), the control unit 18 proceeds to step S202. On the other hand, when not determining that one frame of the irregular interval data string is input (step S201: NO), the control unit 18 repeats step S201.

Subsequently, the correlation-matrix calculating unit 141 calculates a correlation matrix in each processing block (step S202), and calculates a correlation matrix of each sample point by the interpolation processing (step S203). The filter-matrix calculating unit 142 calculates L sets of an eigenvalue and an eigenvector from the correlation matrix for each sample point (step S204).

The filter-matrix calculating unit 142 then determines the number of ranks to be reduced for each sample point (step S205), and calculates an MTI filter matrix for each sample point (step S206). The MTI-filter processing unit 143 performs MTI filter processing (step S207), and the estimating unit 144 performs autocorrelation operation processing using output data that is output by the MTI filter processing (step S208). The estimating unit 144 estimates blood flow information from a result of the autocorrelation operation processing (step S209).

The image generating unit 15 generates color Doppler image data from the blood flow information (step S210), and the monitor 2 displays the color Doppler image data, controlled by the control unit 18 (step S211), and the processing is ended.

As described above, in the second embodiment, by calculating a correlation function of each of subdivision processing blocks by the interpolation processing using a correlation matrix of each of processing blocks, an MTI filter matrix that is optimized for each of subdivision processing blocks can be calculated. As a result, in the second embodiment, even when movement of a tissue greatly differs depending on a position, Doppler image data in which a motion artifact is significantly suppressed can be generated and displayed.

When the interpolation processing explained in the second embodiment is performed, the first ultrasonic scan for Doppler may be performed in a scan form other than the high-frame-rate ultrasonic scan. That is, in the second embodiment, as long as a data string of reflected wave data enabling estimation of blood flow information can be collected, an arbitrary scan form can be applied. For example, even when an alternate scan is performed, by performing the interpolation processing explained in the second embodiment, occurrence of an artifact originated from scan blocks or processing blocks can be significantly suppressed.

In such a case, the correlation-matrix calculating unit 141 divides a scan range in which transmission and reception of ultrasonic waves are performed in an arbitrary scan form into multiple processing blocks, and calculates a correlation matrix of each of the processing blocks from a data string of reflected wave data at an identical position collected in each range. Subsequently, the correlation-matrix calculating unit 141 further calculates a correlation matrix of each of multiple subdivision processing blocks by the interpolation processing using the correlation matrix of each of the processing blocks. The filter-matrix calculating unit 142 performs principal component analysis using a corresponding correlation matrix in each of subdivided ranges, and calculates a filter coefficient to suppress clutter from a tissue by performing a matrix operation to approximate and reduce a clutter component as a principal component, in each of the subdivided ranges. Specifically, the filter-matrix calculating unit 142 calculates an eigenvalue and an eigenvector corresponding to the eigenvalue of a corresponding correlation matrix in each of the subdivision processing blocks, and calculates a matrix in which the rank of a matrix in which respective eigenvectors are aligned based on the magnitude of respective eigenvalues is reduced, as an MTI filter matrix to suppress a clutter component. Thus, the filter-matrix calculating unit 142 calculates a filter matrix of each of the subdivision processing blocks.

The case in which the image processing method explained in the first to the second embodiments is performed in the ultrasonic diagnostic apparatus has been explained. However, the image processing method explained in the first to the second embodiment may be performed in an image processing apparatus that can acquire reflected wave data (IQ data) that is output by the transceiving unit 11.

Moreover, in the above embodiments, the respective components in the respective apparatuses shown are of functional concept, and it is not necessarily required to be physically configured as shown in the drawings. Specifically, a specific form of distribution and integration of the respective devices are not limited to the ones shown in the drawings, and it can be configured such that all or a part thereof is functionally or physically distributed or integrated in arbitrary units according to various kinds of load and usage condition and the like. Furthermore, as for the respective processing functions of the respective devices, all or an arbitrary part thereof can be implemented by a central processing unit (CPU) and a computer program that is analyzed and executed by the CPU, or can be implemented as hardware by wired logic.

Moreover, the image processing method explained in the first to the second embodiments can be implemented by a computer such as a personal computer and a work station. This image processing program can be distributed through a network such as the Internet. Furthermore, this image processing program, can be stored in a computer-readable non-temporary recording medium such as a hard disk, a flexible disk (FD), a compact-disc read-only memory (CD-ROM), a magneto optical disk (MO), a digital versatile disc (DVD), and a flash memory like a universal serial bus (USB) memory and an SD card, and can be executed by being read by a computer from the non-temporary recording medium.

Another Embodiment

Figure 12:
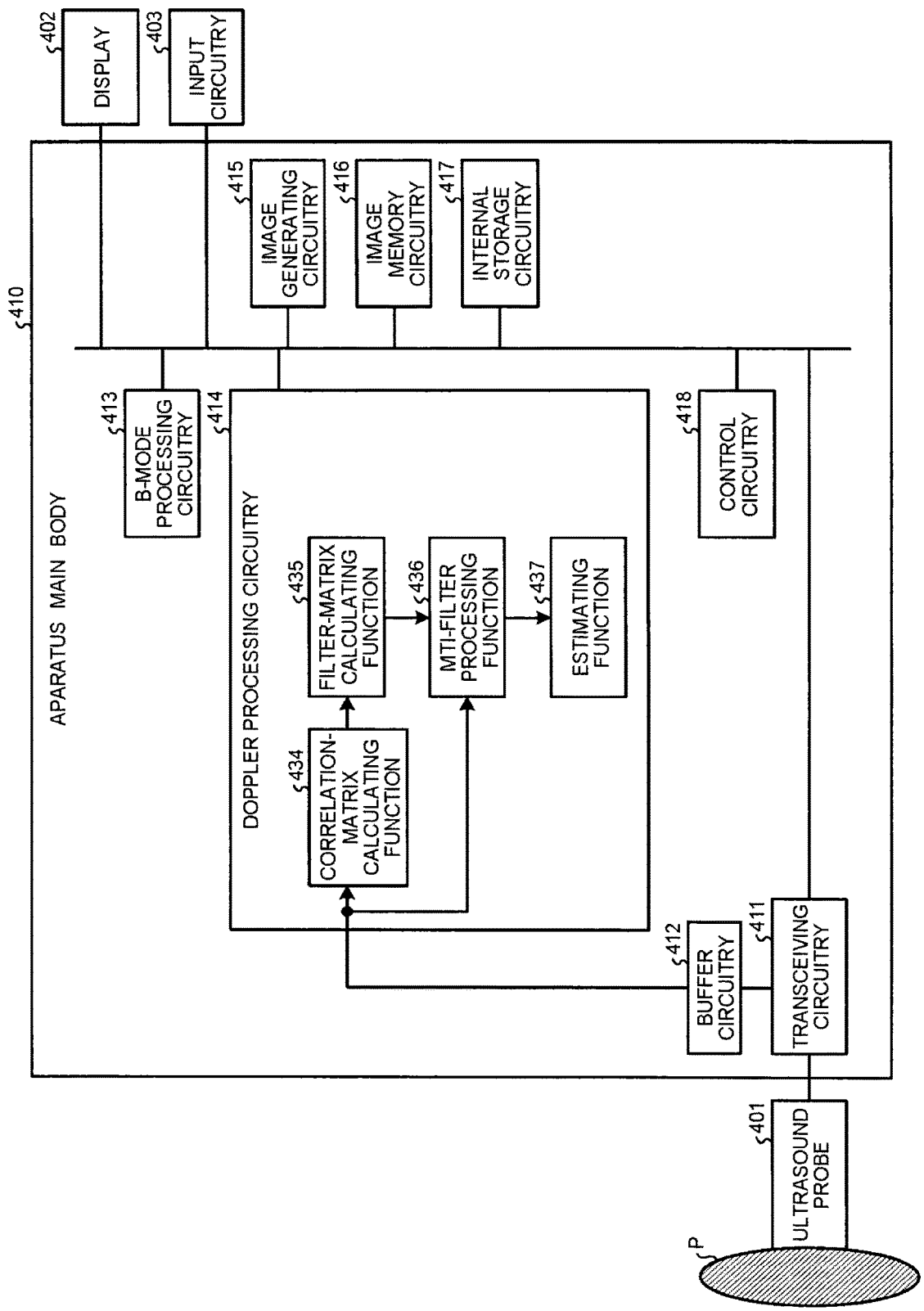
FIG. 12 is a diagram that illustrates an example of the configuration of an ultrasonic diagnostic apparatus according to another embodiment.

The ultrasonic diagnostic apparatus illustrated in the description of the first embodiment and the second embodiment may be configured as illustrated in FIG. 12, for example. FIG. 12 is a diagram that illustrates an example of the configuration of an ultrasonic diagnostic apparatus according to another embodiment.

As illustrated in FIG. 12, the ultrasonic diagnostic apparatus according to the other embodiment includes an ultrasound probe 401, a display 402, an input circuitry 403, and an apparatus main body 410. The ultrasound probe 401, the display 402, the input circuitry 403, and the apparatus main body 410 correspond to the ultrasound probe 1, the monitor 2, the input device 3, and the apparatus main unit 10 illustrated in FIG. 1, respectively.

As illustrated in FIG. 12, the apparatus main body 410 includes a transceiving circuitry 411, a buffer circuitry 412, a B-mode processing circuitry 413, a Doppler processing circuitry 414, an image generating circuitry 415, an image memory circuitry 416, an internal storage circuitry 417, and a control circuitry 418. The transceiving circuitry 411, the buffer circuitry 412, and the B-mode processing circuitry 413 correspond to the transceiving unit 11, the buffer 12, and the B-mode processing unit 13 illustrated in FIG. 1, respectively. The image generating circuitry 415 corresponds to the image generating unit 15 illustrated in FIG. 1 and performs the processing at Step S109 illustrated in FIG. 8. The image generating circuitry 415 is an example of image generating circuitry described in the accompanying claims. The image memory circuitry 416 and the internal storage circuitry 417 correspond to the image memory 16 and the internal storage unit 17 illustrated in FIG. 1, respectively. The control circuitry 418 corresponds to the control unit 18 illustrated in FIG. 1 and performs the processing at Step S110 illustrated in FIG. 8. The control circuitry 418 is an example of control circuitry described in the accompanying claims.

The Doppler processing circuitry 414 corresponds to the Doppler processing unit 14 illustrated in FIG. 1 and performs a correlation-matrix calculating function 434, a filter-matrix calculating function 435, an MTI-filter processing function 436, and an estimating function 437. The Doppler processing circuitry 414 is an example of Doppler processing circuitry described in the accompanying claims. The correlation-matrix calculating function 434 is a function implemented by the correlation-matrix calculating unit 141 illustrated in FIG. 1. The filter-matrix calculating function 435 is a function implemented by the filter-matrix calculating unit 142 illustrated in FIG. 1. The MTI-filter processing function 436 is a function implemented by the MTI-filter processing unit 143 illustrated in FIG. 1. The estimating function 437 is a function implemented by the estimating unit 144 illustrated in FIG. 1.

For example, each of the respective processing functions performed by the correlation-matrix calculating function 434, the filter-matrix calculating function 435, the MTI-filter processing function 436, and the estimating function 437 which are components of the Doppler processing circuitry 414 illustrated in FIG. 12, is stored in the internal storage circuitry 417 in a form of a computer-executable program. The Doppler processing circuitry 414 is a processor that loads programs from the internal storage circuitry 417 and executes the programs so as to implement the respective functions corresponding to the programs. In other words, the Doppler processing circuitry 414 that has loaded the programs has the functions illustrated in the Doppler processing circuitry 414 in FIG. 12. That is, the Doppler processing circuitry 414 loads a program corresponding to the correlation-matrix calculating function 434 from the internal storage circuitry 417 and executes the program so as to perform the same processing as that of the correlation-matrix calculating unit 141. The Doppler processing circuitry 414 loads a program corresponding to the filter-matrix calculating function 435 from the internal storage circuitry 417 and executes the program so as to perform the same processing as that of the filter-matrix calculating unit 142. The Doppler processing circuitry 414 loads a program corresponding to the MTI-filter processing function 436 from the internal storage circuitry 417 and executes the program so as to perform the same processing as that of the MTI-filter processing unit 143. The Doppler processing circuitry 414 loads a program corresponding to the estimating function 437 from the internal storage circuitry 417 and executes the program so as to perform the same processing as that of the estimating unit 144.

For example, Step S102 illustrated in FIG. 8 is a step that is implemented by the Doppler processing circuitry 414 loading the program corresponding to the correlation-matrix calculating function 434 from the internal storage circuitry 417 and executing the program. Step S103 to step S105 illustrated in FIG. 8 is a step that is implemented by the Doppler processing circuitry 414 loading the program corresponding to the filter-matrix calculating function 435 from the internal storage circuitry 417 and executing the program. Step S106 illustrated in FIG. 8 is a step that is implemented by the Doppler processing circuitry 414 loading the program corresponding to the MTI-filter processing function 436 from the internal storage circuitry 417 and executing the program. Step S107 to step S108 illustrated in FIG. 8 is a step that is implemented by the Doppler processing circuitry 414 loading the program corresponding to the estimating function 437 from the internal storage circuitry 417 and executing the program.

In FIG. 12, the correlation-matrix calculating function 434, the filter-matrix calculating function 435, the MTI-filter processing function 436, and the estimating function 437 are described as being implemented in the single Doppler processing circuitry 414. The functions, however, may be implemented by configuring processing circuitry by combining a plurality of separate processors and causing each of the processors to execute a program.

The term "processor" used in the above description means, for example, a central preprocess unit (CPU) and a graphics processing unit (GPU), or circuitry such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in storage circuitry. Instead of being stored in storage circuitry, the program may be built directly in circuitry of the processor. In this case, the processor implements a function by loading and executing the program built in the circuitry. The processors in the present embodiment are not limited to a case in which each of the processors is configured as a single circuit. A plurality of separate circuits may be combined as one processor that implements the respective functions. Furthermore, the components illustrated in FIG. 12 may be integrated into one processor that implements the respective functions.

According to at least one of the embodiments explained above, a motion artifact can be reduced in the color Doppler method in which an irregular interval data string is input.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
a Doppler processing circuitry configured to
calculate a correlation matrix using a first data string that is a set of reflected wave data generated based on reflected waves that are generated by transmitting ultrasonic waves without making time intervals of transmission pulses uniform on an identical scan line;

calculate a filter coefficient based on a result of principal component analysis using the correlation matrix;
extract a second data string that is included in the first data string, and that is a set of reflected wave data originated from reflected waves of the ultrasonic waves that are reflected on a moving object present on the identical scan line, using the filter coefficient;
estimate moving object information of the moving object based on the extracted second data string;
an image generating circuitry configured to generate ultrasonic image data based on the moving object information; and
a control circuitry configured to cause a display to display the ultrasonic image data thereon, wherein
the Doppler processing circuitry determines a number of principal components to be suppressed in the principal component analysis, based on a threshold that is changed in accordance with a magnitude of an eigenvalue of the correlation matrix.

2. The ultrasonic diagnostic apparatus according to claim 1, wherein
the Doppler processing circuitry calculates a power of the moving object using at least a part of the second data string, as the moving object information.

3. The ultrasonic diagnostic apparatus according to claim 1, wherein
the Doppler processing circuitry calculates a speed of the moving object from a pulse pair having a short intervals in the second data string, as the moving object information.

4. The ultrasonic diagnostic apparatus according to claim 2, wherein
the Doppler processing circuitry calculates a speed of the moving object from a pulse pair having a short intervals in the second data string, as the moving object information.

5. An ultrasonic diagnostic apparatus comprising:
a Doppler processing circuitry configured to
calculate a correlation matrix using a first data string that is a set of reflected wave data generated based on reflected waves that are generated by transmitting ultrasonic waves without making time intervals of transmission pulses uniform on an identical scan line;
calculate a filter coefficient based on a result of principal component analysis using the correlation matrix;
extract a second data string that is included in the first data string, and that is a set of reflected wave data originated from reflected waves of the ultrasonic waves that are reflected on a moving object present on the identical scan line, using the filter coefficient;
estimate moving object information of the moving object based on the extracted second data string;
an image generating circuitry configured to generate ultrasonic image data based on the moving object information; and
a control circuitry configured to cause a display to display the ultrasonic image data thereon, wherein
the Doppler processing circuitry determines a number of principal components to be suppressed in the principal component analysis by an adaptive algorithm, based on a magnitude of an eigenvalue of the correlation matrix, and
the Doppler processing circuitry
calculates a correlation matrix in each of a plurality of ranges that are obtained by dividing a scan range in which transmission and reception of ultrasonic waves are performed, and calculates a correlation matrix of each of a plurality of subdivided ranges that are obtained by further dividing each of the ranges by interpolation processing using the correlation matrix of each of the ranges,
calculates a filter coefficient of each of the subdivided ranges from the correlation matrix of each of the subdivided ranges,
extracts the second data string of each of the subdivided ranges using the filter coefficient of each of the subdivided ranges,
estimates the moving object information based on the second data string of each of the subdivided ranges, and
the image generating circuitry generates ultrasonic image data from the moving object information.

6. An image processing apparatus comprising:
a Doppler processing circuitry configured to
calculate a correlation matrix using a first data string that is a set of reflected wave data generated based on reflected waves that are generated by transmitting ultrasonic waves without making time intervals of transmission pulses uniform on an identical scan line;
calculate a filter coefficient based on a result of principal component analysis using the correlation matrix;
extract a second data string that is included in the first data string, and that is a set of reflected wave data originated from reflected waves of the ultrasonic waves that are reflected on a moving object present on the identical scan line, using the filter coefficient;
estimate moving object information of the moving object based on the extracted second data string;
an image generating circuitry configured to generate ultrasonic image data based on the moving object information; and
a control circuitry configured to cause a display to display the ultrasonic image data thereon, wherein
the Doppler processing circuitry determines a number of principal components to be suppressed in the principal component analysis, based on a threshold that is changed in accordance with a magnitude of an eigenvalue of the correlation matrix.

7. An image processing method comprising:
calculating a correlation matrix using a first data string that is a set of reflected wave data generated based on reflected waves that are generated by transmitting ultrasonic waves without making time intervals of transmission pulses uniform on an identical scan line;
calculating a filter coefficient based on a result of principal component analysis using the correlation matrix;
extracting a second data string that is included in the first data string, and that is a set of reflected wave data originated from reflected waves of the ultrasonic waves that are reflected on a moving object present on the identical scan line, using the filter coefficient;
estimating moving object information of the moving object based on the extracted second data string;
generating ultrasonic image data based on the moving object information; and
displaying the ultrasonic image data on a display, wherein
the calculating the filter component comprises determining a number of principal components to be suppressed in the principal component analysis, based on a threshold that is changed in accordance with a magnitude of an eigenvalue of the correlation matrix.

8. The ultrasonic diagnostic apparatus according to claim 1, wherein the Doppler processing circuitry is further configured to calculate the filter coefficient by performing a matrix operation to approximate and reduce a clutter component as a principal component.

9. The ultrasound diagnostic apparatus according to claim 1, wherein the Doppler processing circuitry determines the number of principal components to be suppressed in the principal component analysis by an adaptive algorithm.

* * * * *